US012642826B2

(12) United States Patent  
Kaznessis et al.

(10) Patent No.: US 12,642,826 B2  
(45) Date of Patent: Jun. 2, 2026

(54) COMBINATIONS OF ENGINEERED ANTIMICROBIAL PROBIOTICS FOR TREATMENT OF GASTROINTESTINAL TRACT PATHOGENS

(71) Applicant: General Probiotics, Inc., St. Paul, MN (US)

(72) Inventors: Yiannis John Kaznessis, New Brighton, MN (US); Kathryn Gayle Kruziki, New Brighton, MN (US); Dimitrios Nikolaos Sidiropoulos, Minneapolis, MN (US)

(73) Assignee: General Probiotics, Inc., St. Paul, MN (US)

( * ) Notice: Subject to any disclaimer, the term of this patent is extended or adjusted under 35 U.S.C. 154(b) by 1303 days.

(21) Appl. No.: 17/418,124

(22) PCT Filed: Dec. 23, 2019

(86) PCT No.: PCT/US2019/068400  
§ 371 (c)(1),  
(2) Date: Jun. 24, 2021

(87) PCT Pub. No.: WO2020/139852  
PCT Pub. Date: Jul. 2, 2020

(65) Prior Publication Data

US 2022/0054562 A1 Feb. 24, 2022

Related U.S. Application Data

(60) Provisional application No. 62/785,954, filed on Dec. 28, 2018.

(51) Int. Cl.  
*A61K 35/747* (2015.01)  
*A61K 35/741* (2015.01)  
(Continued)

(52) U.S. Cl.  
CPC .......... *A61K 35/747* (2013.01); *A61K 35/741* (2013.01); *A61K 35/742* (2013.01);  
(Continued)

(58) Field of Classification Search  
None  
See application file for complete search history.

(56) References Cited

U.S. PATENT DOCUMENTS 7,754,469 B2 7/2010 Baltzley et al.  
9,050,281 B2 6/2015 Lang et al.  
(Continued)

FOREIGN PATENT DOCUMENTS

WO 2007025333 3/2007  
WO 2010112861 10/2010  
(Continued)

OTHER PUBLICATIONS

Moreno ("The regulation of microcin B, C, and J operons", Biochimie, 84 (2002), 521-529) (Year: 2002).*  
(Continued)

*Primary Examiner* — Robert J Yamasaki  
*Assistant Examiner* — Charles Zoltan Constantine  
(74) *Attorney, Agent, or Firm* — Pauly, De Vries Smith & Deffner LLC

(57) ABSTRACT

Embodiments herein relate to engineered antimicrobial probiotics for the treatment of gastrointestinal tract pathogens. In an embodiment, a composition for treatment of an animal is included. The composition can include a first genetically engineered bacterium comprising a first exogenous polynucleotide. The first exogenous polynucleotide can include a first heterologous promoter and a first polynucleotide that encodes a first antimicrobial protein. The composition can also include a second genetically engineered bacterium comprising a second exogenous polynucleotide. The second  
(Continued)

Native MJ25 Production System

Promoters and their Regulation  
1. pmjA: nutrient dependent  
2. pmjBCD: nutrient dependent exogenous polynucleotide can include a second heterologous promoter and a second polynucleotide that encodes a second antimicrobial protein. The first heterologous promoter can be induced by one set of exogenous environmental conditions found in the gastrointestinal tract of the animal and the second heterologous promoter can be induced by a second set of exogenous environmental conditions found in the gastrointestinal tract of the animal. Other embodiments are also included herein.

13 Claims, 12 Drawing Sheets

Specification includes a Sequence Listing.

(51) Int. Cl.

| | |
|---|---|
| *A61K 35/742* | (2015.01) |
| *A61K 35/744* | (2015.01) |
| *A61K 35/745* | (2015.01) |
| *A61K 38/16* | (2006.01) |
| *A61P 31/04* | (2006.01) |

(52) U.S. Cl.
CPC .......... *A61K 35/744* (2013.01); *A61K 35/745* (2013.01); *A61K 38/164* (2013.01); *A61P 31/04* (2018.01)

(56) References Cited

U.S. PATENT DOCUMENTS

| | | | | |
|---|---|---|---|---|
| 9,925,223 | B2 | 3/2018 | Kaznessis et al. | |
| 10,813,956 | B2 | 10/2020 | Kaznessis et al. | |
| 11,533,915 | B2 | 12/2022 | Kaznessis et al. | |
| 2014/0314830 | A1* | 10/2014 | Gunzer .................. | A61P 35/00 514/19.2 |
| 2016/0279175 | A1 | 9/2016 | Kaznessis et al. | |
| 2018/0104285 | A1* | 4/2018 | Langella ............... | C07K 14/52 |
| 2018/0264078 | A1 | 9/2018 | Call et al. | |
| 2019/0320683 | A1 | 10/2019 | Connerton et al. | |
| 2020/0299665 | A1 | 9/2020 | Kaznessis et al. | |
| 2021/0268034 | A1 | 9/2021 | Kaznessis et al. | |

FOREIGN PATENT DOCUMENTS

| | | |
|---|---|---|
| WO | 2014121301 | 8/2014 |
| WO | 2014133323 | 9/2014 |
| WO | 2016210373 | 12/2016 |
| WO | 2019051179 | 3/2019 |
| WO | 2019121983 | 6/2019 |
| WO | 2020139852 | 7/2020 |
| WO | 2021154872 | 8/2021 |

OTHER PUBLICATIONS

Fang ("Influence of aeration and carbon source on production of microcin B17 by *Escerichia coli* ZK650", Applied Microbiology and Biotechnology, 1997, 547-553) (Year: 1997).*

"Final Office Action," for U.S. Appl. No. 17/160,132 mailed Aug. 24, 2023 (15 pages).

"Notice of Allowance," for U.S. Appl. No. 17/160,132 mailed Jun. 11, 2024 (9 pages).

"Response to Final Office Action," for U.S. Appl. No. 17/160,132, filed Feb. 26, 2024 (8 pages).

Dombek, et al., "Use of Repetitive DNA Sequences and the PCT To Differentiate *Escherichia coli* Isolates from Human and Animal Sources," Jun. 2000, Applied and Environmental Microbiology, vol. 66, No. 6, p. 2572-2577 (6 pages).

"International Preliminary Report on Patentability," for PCT Application No. PCT/US2019/068400 mailed Jul. 8, 2021 (8 pages).

"International Search Report and Written Opinion," for PCT Application No. PCT/US2019/068400 mailed Apr. 9, 2020 (15 pages).

"International Search Report and Written Opinion," for PCT Application No. PCT/US2021/015313 mailed Apr. 20, 2021 (25 pages).

Bajagai, Yadav, et al. "Probiotics in Animal Nutrition-Production, Impact and Regulation," FAO. 2016. Animal Production and Health Paper No. 179. Rome (108 pages).

Borrero, Juan, et al. "Modified Lactic Acid Bacteria Detect and Inhibit Multiresistant Enterococci," ACS Synth. Biol. 2015, 4, 299-306 (8 pages).

Chiuchiolo, M. J., et al. "Growth-Phase-Dependent Expression of the Cyclopeptide Antibiotic Microcin J25," J. Bacteriol. Mar. 2001; 183(5): 1755-1764 (10 pages).

Coman, M. M., et al. "In vitro evaluation of antimicrobial activity of Lactobacillus rhamnosus IMC 501, Lactobacillus paracasei IMC 502 and SYNBIO against pathogens," Journal of Applied Microbiology, vol. 117, No. 2, Jun. 3, 2014, pp. 518-527 (10 pages).

Forkus, Brittany, et al. "Antimicrobial Probiotics Reduce Salmonella enterica in Turkey Gastrointestinal Tracts," Scientific Reports, vol. 7, No. 1, Jan. 17, 2017 (10 pages).

Geldart, Kathryn, et al. "Chloride-Inducible Expression Vector for Delivery of Antimicrobial Peptides Targeting Antibiotic-Resistant Enterococcus Faecium," Applied and Environmental Microbiology, Jun. 2015, vol. 81, No. 11, pp. 3889-3897 (9 pages).

Jayaraman, P., et al. "Repurposing a Two-Component System-Based Biosensor for the Killing of Vibrio cholerae," ACS Synth Biol. Jul. 21, 2017;6(7):1403-1415 (27 pages).

Mutalik, Vivek, et al. "Precise and reliable gene expression via standard transcription and translation initiation elements," Nature Methods. 2013, 10(4):354-360 (15 pages).

Nissen-Meyer, Jon, et al. "Robosomally synthesized antimicrobial peptides: their function, structure, biogenesis, and mechanism of action," Arch. Microbiol (1997) 167: 67-77 (11 pages).

Piraner, D. I., et al. "Tunable thermal bioswitches for in vivo control of microbial therapeutics," Nat. Chem. Biol. Jan. 2017; 13(1):75-80 (9 pages).

Prescott, J.F., et al. "The pathogenesis of necrotic enteritis in chickens: what we know and what we need to know: a review," Avian Pathology, 45(3), 2016, 288-294 (8 pages).

Prindle, Arthur, et al. "A sensing array of radically coupled genetic 'biopixels'," Nature 2011, Published Dec. 18, 2011 (6 pages).

Sanders, J. W., et al. "A chloride-inducible gene expression cassette and its use in induced lysis of Lactococcus lactis.," Appl. Environ. Microbiol. Dec. 1997;63(12):4877-82 (6 pages).

Volzing, Katherine, et al. "Antimicrobial Peptides Targeting Gram-negative Pathogens, Produced and Delivered by Lactic Acid Bacteria," ACS Synthetic Biology, vol. 2, No. 11, Jul. 10, 2013, pp. 643-640 (8 pages).

"International Preliminary Report on Patentability," for PCT Application No. PCT/US2021/015313 mailed Aug. 11, 2022 (18 pages).

"Non-Final Office Action," for U.S. Appl. No. 17/160,132 mailed Jan. 11, 2023 (31 pages).

"Response to Non-Final Office Action," for U.S. Appl. No. 17/160,132, filed Jul. 11, 2023 (12 pages).

McClure, William R." Mechanism and Control of Transcription Initiation in Prokaryotes," Annual Reviews Biochemistry, 1985, vol. 54, p. 171-204 (37 pages).

\* cited by examiner

Native MJ25 Production System

Promoters and their Regulation
1. pmjA: nutrient dependent
2. pmjBCD: nutrient dependent Salomonella growth Engineered EcN Zone of inhibition

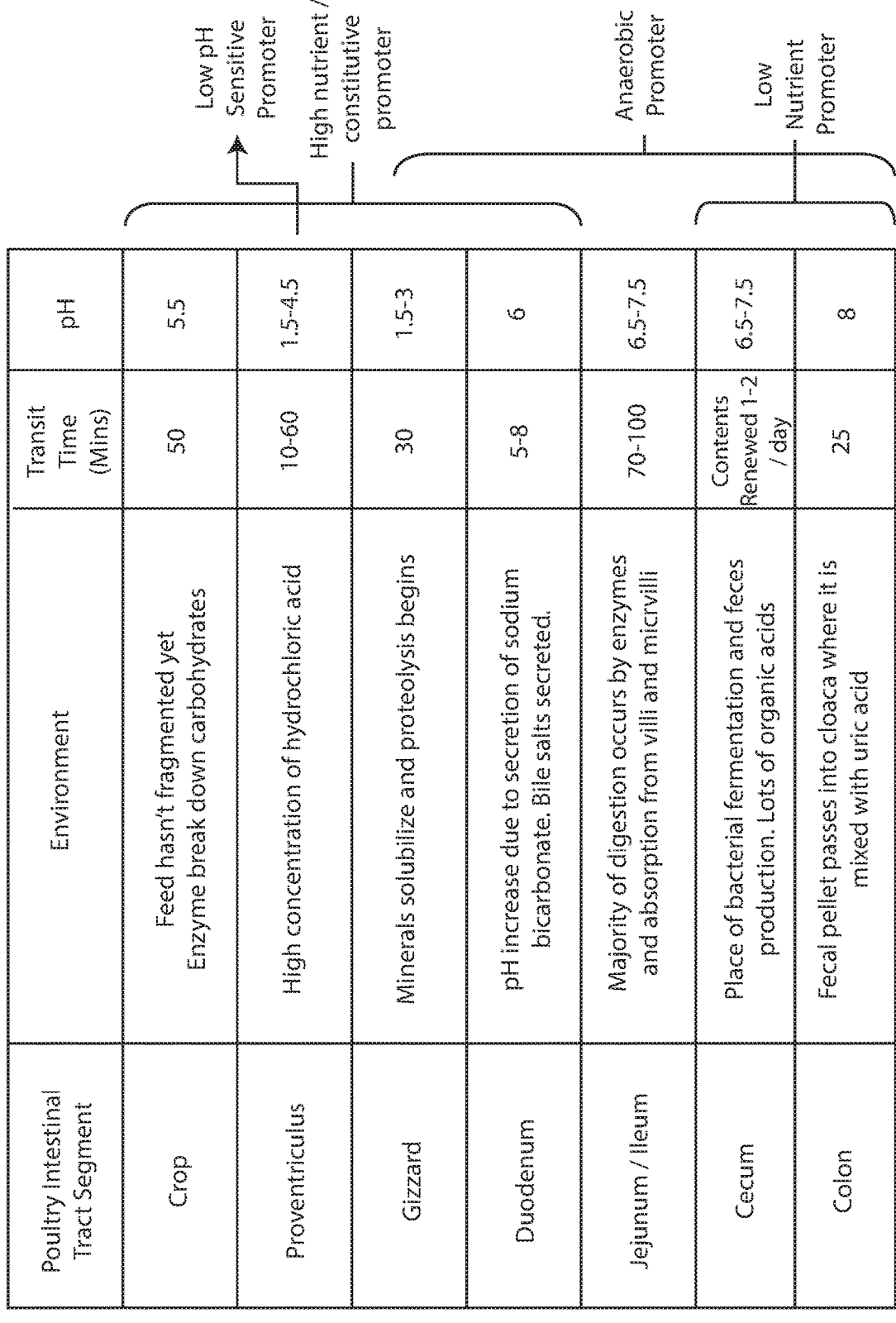

| Poultry Intestinal Tract Segment | Environment | Transit Time (Mins) | pH |
|---|---|---|---|
| Crop | Feed hasn't fragmented yet Enzyme break down carbohydrates | 50 | 5.5 |
| Proventriculus | High concentration of hydrochloric acid | 10-60 | 1.5-4.5 |
| Gizzard | Minerals solubilize and proteolysis begins | 30 | 1.5-3 |
| Duodenum | pH increase due to secretion of sodium bicarbonate. Bile salts secreted. | 5-8 | 6 |
| Jejunum / Ileum | Majority of digestion occurs by enzymes and absorption from villi and micrvilli | 70-100 | 6.5-7.5 |
| Cecum | Place of bacterial fermentation and feces production. Lots of organic acids | Contents Renewed 1-2 / day | 6.5-7.5 |
| Colon | Fecal pellet passes into cloaca where it is mixed with uric acid | 25 | 8 |

Low pH Sensitive Promoter

High nutrient / constitutive promoter

Anaerobic Promoter

Low Nutrient Promoter

O₂

Oxygen decreases, intestinal gases increase.

FIG. 12

SEQUENCE LISTING

<160> NUMBER OF SEQ ID NOS: 41

<210> SEQ ID NO 1
<211> LENGTH: 177
<212> TYPE: DNA
<213> ORGANISM: Escherichia coli

<400> SEQUENCE: 1

```
atgattaagc attttcattt taataaactg tcttctggta aaaaaaataa tgttccatct       60
cctgcaaagg gggttataca aataaaaaaa tcagcatcgc aactcacaaa aggtggtgca      120
```

-continued

```
ggacatgtgc ctgagtattt tgtggggatt ggtacaccta tatctttcta tggctga          177

<210> SEQ ID NO 2
<211> LENGTH: 3916
<212> TYPE: DNA
<213> ORGANISM: Escherichia coli

<400> SEQUENCE: 2
atgatccgtt actgcttaac cagttataga gaggatcttg ttatcctgga tataattaat        60
gatagtttca gcatagtgcc tgacgcaggt agcttgctaa aagaaagaga taaattgctt       120
aaagaattcc cacaactatc ttactttttt gacagtgaat atcatattgg aagtgtttct       180
cgtaatagtg acacttcttt tcttgaagaa cgctggtttc taccagaacc tgacaaaaca       240
ttatataagt gttctctatt taaacgattt atattattac tcaaagtctt ttactatagc       300
tggaatattg aaaaaaaagg gatggcatgg attttcataa gtaataaaaa agagaatagg       360
ctatactcct tgaatgaaga gcatcttatc cggaaagaaa ttagtaatct ttccattatc       420
tttcatctta atatttttaa atctgactgt cttacctatt catacgcact aaaaagaatt       480
cttaattcca gaaatattga tgctcatctt gttattggtg taaggacaca acctttttat       540
agccactctt gggtggaggt tgggggacaa gttatcaatg atgctcccaa tatgcgggat       600
aaattatctg ttattgcaga gatatagtta tggaaatatt taatgtcaag ttaaatgata       660
cttcaattag aattattttc tgtaaaacgc tttctgcctt ccggacagaa aataccatcg       720
ttatgctcaa aggaaaagca gtttcaaatg gcaaacctgt atccacagag gagattgcca       780
gagtagtgga agaaaaaggt gtttcagaag taatagaaaa tttagatggt gttttctgta       840
tcctaattta tcattttaat gatctcctta tagggaaaag cattcaatca ggccccgctc       900
tattttattg taaaaagaat atggatattt ttgtttcgga taaaatttct gatatcaaat       960
ttttgaatcc agatatgaca ttcagtctaa atataacaat ggcagaacat tatctgtcag      1020
gaaatcgaat agcaacccag gaatcactaa tcactggcat ttacaaagta aataatggtg      1080
agtttataaa atttaataat cagttgaaac ctgtgctact tcgtgatgag tttagtatta      1140
ccaaaaagaa caattcaact atcgacagta tcattgataa tattgagatg atgcgggata      1200
atagaaaaat agccctatta ttttccggag gattggattc tgcattaatt tttcacacac      1260
ttaaagaatc aggtaacaaa ttctgcgctt atcatttttt ttctgatgaa tctgatgaca      1320
gtgaaaagta ttttgctaag gaatactgtt caaaatatgg agttgatttt atatctgtta      1380
ataaaaacat caactttaat gaaaaacttt atttcaattt aaatcctaat agtccggacg      1440
aaatcccttt gatatttgaa cagacagatg aagaaggtga aggtcagccc cccatagacg      1500
atgatttatt atatctatgt ggtcacggtg gagatcatat tttcggacaa aatccttcag      1560 aacttttttgg cattgatgca tatcgaagtc atggcttgat gtttatgcat aaaaaaatag      1620
tagaattttc caatctcaag ggaaagagat ataaagatat catattttca aatatttccg      1680
cattcattaa tacatccaac ggatgttctc cagcaaagca agagcacgta tcagatatga      1740
aacttgcctc tgctcagttt tttgcaactg attatacagg aaaaattaat aaactaactc      1800
cattcctgca taaaaatatt atccagcatt atgctggctt accagttttt agtctattta      1860
accagcactt tgatcgttat cccgttcgtt atgaagcgtt tcaacgattt ggttcagata      1920
ttttctggaa aaaaaccaaa cggtcatctt cacagctaat attcagaatt ctatccggta      1980
aaaaggatga actagtgaat acaataaaac agtcaggatt aattgaaata ttaggcatta      2040
```

-continued

```
accatattga attggaaagc attttgtatg aaaatacgac tacacgtctg acaatggaac        2100
taccatatat acttaactta taccgtctgg caaaattcat tcaacttcaa tccattgatt        2160
ataaaggtta attatggaaa gaaaacagaa aaactcatta tttaattata tttattcatt        2220
aatggatgta agaggtaaat ttttattctt ttccatgtta ttcattacat cattatcatc        2280
gataatcata tctatttcac cattgattct tgcaaagatt acagatttac tgtctggctc        2340
attgtcaaat tttagttatg aatatctggt tttacttgcc tgtttataca tgttttgcgt        2400
tatatctaat aaagcaagtg ttttttttatt tatgatactg caaagtagtc tacgtattaa       2460
catgcagaaa aaaatgtcgc taaagtattt gagagaattg tataacgaaa atataactaa        2520
cttgagtaaa aataatgctg gatatacaac gcaaagtctt aaccaggctt caaatgacat        2580
ttatattctt gtgagaaatg tttcccagaa tatcctgtca cctgttatac aacttatttc        2640
cactattgtt gttgtttat ctacgaagga ctggttttct gccggtgtgt ttttttctcta        2700 tattctggta tttgtaattt ttaataccag actgactggc agtttagcgt ctctcagaaa        2760
acacagcatg gatatcactc ttaactctta tagtctgtta tctgatactg ttgataacat        2820
gatagcagct aaaaagaata atgcattaag acttatttct gaacgttatg aagatgctct        2880
cactcaggaa aacaatgctc agaaaaaata ctggttactc agttctaaag ttcttttatt        2940
gaactcttta cttgctgtaa tattatttgg ttctgtattc atatataata ttttaggtgt        3000
gctgaatggt gtagttagta tcggccactt cattatgatt acatcatata tcattcttct        3060
ttcaacgcca gtggaaaata tagggggcatt gctaagtgag atcaggcagt caatgtctag       3120
cctggcaggt tttattcaac gtcatgccga gaataaagcc acatctcctt caataccttt        3180
tctcaacatg gagcgaaaat taaacctgtc cataagagag ctttcattta gctatagtga        3240
tgataaaaaa atacttaatt cagtcagtct tgacctttt accggaaaaa tgtattcatt         3300
aaccggaccc agtggttcag gaaaatccac ccttgtaaaa ataatatcag gttactataa        3360
aaattacttt ggagacattt atctgaatga tatatcctta cgtaatatca gtgatgagga        3420
tttgaatgat gctatttact acctaacaca agatgattat attttttatgg atacactacg       3480 atttaatctc cggctcgcaa attacgacgc gtcagaaaat gaaatattta agttcttaa         3540 actggcaaat ctttctgtcg tcaacaatga accagtgagt ctggatacac accttataaa        3600
cagaggcaat aactattcag gagggcaaaa acaacgaatt tcgttagcgc gactgttttt        3660
gagaaaacct gcaataatta ttattgatga agccacatcg gctctggatt atattaatga       3720
atcagaaatt ttatcatcaa taagaactca ttttcctgat gcgttaatta taaatattag       3780
tcaccgaata aatcttctgg agtgttccga ttgtgtttat gtattgaatg aaggaaatat        3840
tgttgcttct ggccatttca gggatttgat ggtcagcaat gaatacatat cgggactggc       3900
ttctgttact gaataa                                                       3916
```

<210> SEQ ID NO 3
<211> LENGTH: 35
<212> TYPE: DNA
<213> ORGANISM: Artificial
<220> FEATURE:
<223> OTHER INFORMATION: synthetic promoter J23109

<400> SEQUENCE: 3

```
tttacagcta gctcagtcct agggactgtg ctagc                                    35
```

<210> SEQ ID NO 4
<211> LENGTH: 35

-continued

```
<212> TYPE: DNA
<213> ORGANISM: Artificial
<220> FEATURE:
<223> OTHER INFORMATION: synthetic promoter J23106

<400> SEQUENCE: 4
tttacggcta gctcagtcct aggtatagtg ctagc                              35

<210> SEQ ID NO 5
<211> LENGTH: 35
<212> TYPE: DNA
<213> ORGANISM: Artificial
<220> FEATURE:
<223> OTHER INFORMATION: synthetic promoter J23100

<400> SEQUENCE: 5
ttgacggcta gctcagtcct aggtacagtg ctagc                              35

<210> SEQ ID NO 6
<211> LENGTH: 150
<212> TYPE: DNA
<213> ORGANISM: Escherichia coli

<400> SEQUENCE: 6
agttgttctt attggtggtg ttgctttatg gttgcatcgt agtaaatggt tgtaacaaaa    60
gcaatttttc cggctgtctg tatacaaaaa cgccgtaaag tttgagcgaa gtcaataaac   120
tctctaccca ttcagggcaa tatctctctt                                   150

<210> SEQ ID NO 7
<211> LENGTH: 264
<212> TYPE: DNA
<213> ORGANISM: Escherichia coli

<400> SEQUENCE: 7
ctttcctgca cagtctgaac ggggtgtaca cgccgtatat gcaggataaa caataattaa    60
tttgatcgcc cgaacagcaa tgtttgggcg attttttatta cgataataaa gtctgttttt   120
aatattatca tgttaaatgt ttatattata aaaagtcgtt tttctgctta ggattttgtt   180
atttaaatta agcctgtaat gccttgcttc cattgcggat aaatcctact tttttattgc   240
cttcaaataa atttaaggag ttcg                                         264

<210> SEQ ID NO 8
<211> LENGTH: 231
<212> TYPE: DNA
<213> ORGANISM: Escherichia coli

<400> SEQUENCE: 8
tcaagtacta atagtgatat tttaaggtct gatttttacg tgataattca ggagacacag    60
aatgcgcata aaaataacag cataaaacac cttaccacca cccaagaatt tcatattgta   120
ttgtttttca atgaaaaaat attattcgcg taatatctca cgataaataa cattaggatt   180
ttgttattta aacacgagtc ctttgcactt gcttacttta tcgataaatc c           231

<210> SEQ ID NO 9
<211> LENGTH: 63
<212> TYPE: DNA
<213> ORGANISM: Escherichia coli

<400> SEQUENCE: 9
ccctgcgcgc gagcagattt cacggaataa tttcaccaga cttattctta gctattatag    60
```

-continued

```
tta                                                                        63

<210> SEQ ID NO 10
<211> LENGTH: 441
<212> TYPE: DNA
<213> ORGANISM: Escherichia coli

<400> SEQUENCE: 10
ggagtttttt cttaattgat ggctaaatat tctgaaataa ttagaaaaat gtataaaaat     60
ccaaaatatt gtactaaatt tgaccacttt tgcagattga ttagtttatg gatgtttgta    120
tctaaatgat tttattgata aattactaaa gcgtaatgat tattgatctc aattgtattt    180
tgtgctaata aaattctaac agaaggacgt gaggttcctc tgtaaaaatc atcatactat    240
ttccatcaaa taaggaacgt aaaaatgatt aagcattttc attttaataa actgtcttct    300
ggtaaaaaaa ataatgttcc atctcctgca aaggggggtta tacaaataaa aaaatcagca    360
tcgcaactca caaaaggtgg tgcaggacat gtgcctgagt attttgtggg gattggtaca    420
cctatatctt tctatggctg a                                              441

<210> SEQ ID NO 11
<211> LENGTH: 84
<212> TYPE: DNA
<213> ORGANISM: Artificial
<220> FEATURE:
<223> OTHER INFORMATION: synthetic RBS of bicistronic design by Mutalik
      et al.

<400> SEQUENCE: 11
gggcccaagt tcacttaaaa aggagatcaa caatgaaagc aattttcgta ctgaaacatc     60
ttaatcatgc taaggaggtt ttct                                           84

<210> SEQ ID NO 12
<211> LENGTH: 129
<212> TYPE: DNA
<213> ORGANISM: Artificial
<220> FEATURE:
<223> OTHER INFORMATION: transcriptional terminator

<400> SEQUENCE: 12
ccaggcatca aataaaacga aaggctcagt cgaaagactg ggcctttcgt tttatctgtt     60
gtttgtcggt gaacgctctc tactagagtc acactggctc accttcgggt gggcctttct    120
gcgtttata                                                            129

<210> SEQ ID NO 13
<211> LENGTH: 21
<212> TYPE: PRT
<213> ORGANISM: Escherichia coli

<400> SEQUENCE: 13

Gly Gly Ala Gly His Val Pro Glu Tyr Phe Val Gly Ile Gly Thr Pro
1               5                   10                  15

Ile Ser Phe Tyr Gly
            20

<210> SEQ ID NO 14
<211> LENGTH: 47
<212> TYPE: PRT
<213> ORGANISM: Enterococcus faecium

<400> SEQUENCE: 14
```

```
Thr Thr His Ser Gly Lys Tyr Tyr Gly Asn Gly Val Tyr Cys Thr Lys
1               5                   10                  15

Asn Lys Cys Thr Val Asp Trp Ala Lys Ala Thr Thr Cys Ile Ala Gly
            20                  25                  30

Met Ser Ile Gly Gly Phe Leu Gly Gly Ala Ile Pro Gly Lys Cys
        35                  40                  45
```

```
<210> SEQ ID NO 15
<211> LENGTH: 44
<212> TYPE: PRT
<213> ORGANISM: Enterococcus faecium

<400> SEQUENCE: 15

Ala Thr Arg Ser Tyr Gly Asn Gly Val Tyr Cys Asn Asn Ser Lys Cys
1               5                   10                  15

Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
        35                  40
```

```
<210> SEQ ID NO 16
<211> LENGTH: 53
<212> TYPE: PRT
<213> ORGANISM: Enterococcus faecium

<400> SEQUENCE: 16

Glu Asn Asp His Arg Met Pro Asn Glu Leu Asn Arg Pro Asn Asn Leu
1               5                   10                  15

Ser Lys Gly Gly Ala Lys Cys Gly Ala Ala Ile Ala Gly Gly Leu Phe
            20                  25                  30

Gly Ile Pro Lys Gly Pro Leu Ala Trp Ala Ala Gly Leu Ala Asn Val
        35                  40                  45

Tyr Ser Lys Cys Asn
        50
```

```
<210> SEQ ID NO 17
<211> LENGTH: 44
<212> TYPE: PRT
<213> ORGANISM: Enterococcus hirae

<400> SEQUENCE: 17

Ala Thr Tyr Tyr Gly Asn Gly Leu Tyr Cys Asn Lys Glu Lys Cys Trp
1               5                   10                  15

Val Asp Trp Asn Gln Ala Lys Gly Glu Ile Gly Lys Ile Ile Val Asn
            20                  25                  30

Gly Trp Val Asn His Gly Pro Trp Ala Pro Arg Arg
        35                  40
```

```
<210> SEQ ID NO 18
<211> LENGTH: 18
<212> TYPE: PRT
<213> ORGANISM: Sus scrofa

<400> SEQUENCE: 18

Arg Gly Gly Arg Leu Cys Tyr Cys Arg Arg Arg Phe Cys Val Cys Val
1               5                   10                  15

Gly Arg
```

```
<210> SEQ ID NO 19
<211> LENGTH: 12
```

```
<212> TYPE: PRT
<213> ORGANISM: Artificial
<220> FEATURE:
<223> OTHER INFORMATION: peptide analog of pig protegrin-1 (PG-1)

<400> SEQUENCE: 19

Leu Thr Tyr Cys Arg Arg Arg Phe Cys Val Thr Val
1               5                   10

<210> SEQ ID NO 20
<211> LENGTH: 23
<212> TYPE: PRT
<213> ORGANISM: Alytes obstetricians

<400> SEQUENCE: 20

Gly Leu Lys Asp Ile Phe Lys Ala Gly Leu Gly Ser Leu Val Lys Gly
1               5                   10                  15

Ile Ala Ala His Val Ala Asn
            20

<210> SEQ ID NO 21
<211> LENGTH: 26
<212> TYPE: PRT
<213> ORGANISM: Gallus gallus

<400> SEQUENCE: 21

Arg Val Lys Arg Val Trp Pro Leu Val Ile Arg Thr Val Ile Ala Gly
1               5                   10                  15

Tyr Asn Leu Tyr Arg Ala Ile Lys Lys Lys
            20                  25

<210> SEQ ID NO 22
<211> LENGTH: 74
<212> TYPE: PRT
<213> ORGANISM: Escherichia coli

<400> SEQUENCE: 22

Ala Gly Asp Pro Leu Ala Asp Pro Asn Ser Gln Ile Val Arg Gln Ile
1               5                   10                  15

Met Ser Asn Ala Ala Trp Gly Pro Pro Leu Val Pro Glu Arg Phe Arg
            20                  25                  30

Gly Met Ala Val Gly Ala Ala Gly Gly Val Thr Gln Thr Val Leu Gln
        35                  40                  45

Gly Ala Ala Ala His Met Pro Val Asn Val Pro Ile Pro Lys Val Pro
    50                  55                  60

Met Gly Pro Ser Trp Asn Gly Ser Lys Gly
65                  70

<210> SEQ ID NO 23
<211> LENGTH: 88
<212> TYPE: PRT
<213> ORGANISM: Escherichia coli

<400> SEQUENCE: 23

Ala Ser Gly Arg Asp Ile Ala Met Ala Ile Gly Thr Leu Ser Gly Gln
1               5                   10                  15

Phe Val Ala Gly Gly Ile Gly Ala Ala Ala Gly Gly Val Ala Gly Gly
            20                  25                  30

Ala Ile Tyr Asp Tyr Ala Ser Thr His Lys Pro Asn Pro Ala Met Ser
        35                  40                  45

Pro Ser Gly Leu Gly Gly Thr Ile Lys Gln Lys Pro Glu Gly Ile Pro
```

```
           50                 55                 60

Ser Glu Ala Trp Asn Tyr Ala Ala Gly Arg Leu Cys Asn Trp Ser Pro
65                  70                  75                  80

Asn Asn Leu Ser Asp Val Cys Leu
                85

<210> SEQ ID NO 24
<211> LENGTH: 11
<212> TYPE: PRT
<213> ORGANISM: Lactobacillus acidophilus

<400> SEQUENCE: 24

Asn Val Gly Val Leu Asn Pro Pro Pro Leu Val
1               5                   10

<210> SEQ ID NO 25
<211> LENGTH: 11
<212> TYPE: PRT
<213> ORGANISM: Lactobacillus acidophilus

<400> SEQUENCE: 25

Asn Val Gly Val Leu Asn Pro Pro Met Leu Val
1               5                   10

<210> SEQ ID NO 26
<211> LENGTH: 11
<212> TYPE: PRT
<213> ORGANISM: Lactobacillus acidophilus

<400> SEQUENCE: 26

Asn Val Gly Val Leu Leu Pro Pro Pro Leu Val
1               5                   10

<210> SEQ ID NO 27
<211> LENGTH: 11
<212> TYPE: PRT
<213> ORGANISM: Lactobacillus acidophilus

<400> SEQUENCE: 27

Asn Val Gly Val Leu Leu Pro Pro Met Leu Val
1               5                   10

<210> SEQ ID NO 28
<211> LENGTH: 8
<212> TYPE: PRT
<213> ORGANISM: Lactobacillus rhamnosus

<400> SEQUENCE: 28

Asn Pro Ser Arg Gln Glu Arg Arg
1               5

<210> SEQ ID NO 29
<211> LENGTH: 5
<212> TYPE: PRT
<213> ORGANISM: Lactobacillus rhamnosus

<400> SEQUENCE: 29

Pro Asp Glu Asn Lys
1               5

<210> SEQ ID NO 30
<211> LENGTH: 289
<212> TYPE: PRT
<213> ORGANISM: Enterobacteria phage F1
```

<400> SEQUENCE: 30

Met Ala Gly Glu Val Phe Ser Ser Leu Ile Thr Ser Val Asn Pro Asn
1               5                   10                  15

Pro Met Asn Ala Gly Ser Arg Asn Gly Ile Pro Ile Asp Thr Ile Ile
            20                  25                  30

Leu His His Asn Ala Thr Thr Asn Lys Asp Val Ala Met Asn Thr Trp
        35                  40                  45

Leu Leu Gly Gly Gly Ala Gly Thr Ser Ala His Tyr Glu Cys Thr Pro
    50                  55                  60

Thr Glu Ile Ile Gly Cys Val Gly Glu Gln Tyr Ser Ala Phe His Ala
65                  70                  75                  80

Gly Gly Thr Gly Gly Ile Asp Val Pro Lys Ile Ala Asn Pro Asn Gln
                85                  90                  95

Arg Ser Ile Gly Ile Glu Asn Val Asn Ser Ser Gly Ala Pro Asn Trp
            100                 105                 110

Ser Val Asp Pro Arg Thr Ile Thr Asn Cys Ala Arg Leu Val Ala Asp
            115                 120                 125

Ile Cys Thr Arg Tyr Gly Ile Pro Cys Asp Arg Gln His Val Leu Gly
        130                 135                 140

His Asn Glu Val Thr Ala Thr Ala Cys Pro Gly Gly Met Asp Val Asp
145                 150                 155                 160

Glu Val Val Arg Gln Ala Gln Gln Phe Met Ala Gly Gly Ser Asn Asn
                165                 170                 175

Ala Val Lys Pro Glu Pro Ser Lys Pro Thr Pro Ser Lys Pro Ser Asn
            180                 185                 190

Asn Lys Asn Lys Glu Gly Val Ala Thr Met Tyr Cys Leu Tyr Glu Arg
            195                 200                 205

Pro Ile Asn Ser Lys Thr Gly Val Leu Glu Trp Asn Gly Asp Ala Trp
    210                 215                 220

Thr Val Met Phe Cys Asn Gly Val Asn Cys Arg Arg Val Ser His Pro
225                 230                 235                 240

Asp Glu Met Lys Val Ile Glu Asp Ile Tyr Arg Lys Asn Asn Gly Lys
            245                 250                 255

Asp Ile Pro Phe Tyr Ser Gln Lys Glu Trp Asn Lys Asn Ala Pro Trp
            260                 265                 270

Tyr Asn Arg Leu Glu Thr Val Cys Pro Val Val Gly Ile Thr Lys Lys
        275                 280                 285

Ser

<210> SEQ ID NO 31
<211> LENGTH: 410
<212> TYPE: PRT
<213> ORGANISM: Enterobacteria phage F1

<400> SEQUENCE: 31

Met Ser Asn Ile Asn Met Glu Thr Ala Ile Ala Asn Met Tyr Ala Leu
1               5                   10                  15

Lys Ala Arg Gly Ile Thr Tyr Ser Met Asn Tyr Ser Arg Thr Gly Ala
            20                  25                  30

Asp Gly Thr Gly Asp Cys Ser Gly Thr Val Tyr Asp Ser Leu Arg Lys
        35                  40                  45

Ala Gly Ala Ser Asp Ala Gly Trp Val Leu Asn Thr Asp Ser Met His
    50                  55                  60

-continued

```
Ser Trp Leu Glu Lys Asn Gly Phe Lys Leu Ile Ala Gln Asn Lys Glu
65                  70                  75                  80

Trp Ser Ala Lys Arg Gly Asp Val Val Ile Phe Gly Lys Lys Gly Ala
                85                  90                  95

Ser Gly Gly Ser Ala Gly His Val Val Ile Phe Ile Ser Ser Thr Gln
            100                 105                 110

Ile Ile His Cys Thr Trp Lys Ser Ala Thr Ala Asn Gly Val Tyr Val
        115                 120                 125

Asp Asn Glu Ala Thr Thr Cys Pro Tyr Ser Met Gly Trp Tyr Val Tyr
        130                 135                 140

Arg Leu Asn Gly Gly Ser Thr Pro Pro Lys Pro Asn Thr Lys Lys Val
145                 150                 155                 160

Lys Val Leu Lys His Ala Thr Asn Trp Ser Pro Ser Ser Lys Gly Ala
                165                 170                 175

Lys Met Ala Ser Phe Val Lys Gly Gly Thr Phe Glu Val Lys Gln Gln
                180                 185                 190

Arg Pro Ile Ser Tyr Ser Tyr Ser Asn Gln Glu Tyr Leu Ile Val Asn
                195                 200                 205

Lys Gly Thr Val Leu Gly Trp Val Leu Ser Gln Asp Ile Glu Gly Gly
        210                 215                 220

Tyr Gly Ser Asp Arg Val Gly Gly Ser Lys Pro Lys Leu Pro Ala Gly
225                 230                 235                 240

Phe Thr Lys Glu Glu Ala Thr Phe Ile Asn Gly Asn Ala Pro Ile Thr
                245                 250                 255

Thr Arg Lys Asn Lys Pro Ser Leu Ser Ser Gln Thr Ala Thr Pro Leu
                260                 265                 270

Tyr Pro Gly Gln Ser Val Arg Tyr Leu Gly Trp Lys Ser Ala Glu Gly
                275                 280                 285

Tyr Ile Trp Ile Tyr Ala Thr Asp Gly Arg Tyr Ile Pro Val Arg Pro
        290                 295                 300

Val Gly Lys Glu Ala Trp Gly Thr Phe Lys Gln Asp Ile Glu Gly Gly
305                 310                 315                 320

Tyr Gly Ser Asp Arg Val Gly Gly Ser Lys Pro Lys Leu Pro Ala Gly
                325                 330                 335

Phe Thr Lys Glu Glu Ala Thr Phe Ile Asn Gly Asn Ala Pro Ile Thr
                340                 345                 350

Thr Arg Lys Asn Lys Pro Ser Leu Ser Ser Gln Thr Ala Thr Pro Leu
                355                 360                 365

Tyr Pro Gly Gln Ser Val Arg Tyr Leu Gly Trp Lys Ser Ala Glu Gly
        370                 375                 380

Tyr Ile Trp Ile Tyr Ala Thr Asp Gly Arg Tyr Ile Pro Val Arg Pro
385                 390                 395                 400

Val Gly Lys Glu Ala Trp Gly Thr Phe Lys
                405                 410
```

```
<210> SEQ ID NO 32
<211> LENGTH: 328
<212> TYPE: PRT
<213> ORGANISM: Enterobacteria phage EFAP-1

<400> SEQUENCE: 32

Met Lys Leu Lys Gly Ile Leu Leu Ser Val Val Thr Thr Phe Gly Leu
1               5                   10                  15

Leu Phe Gly Ala Thr Asn Val Gln Ala Tyr Glu Val Asn Asn Glu Phe
            20                  25                  30
```

-continued

```
Asn Leu Gln Pro Trp Glu Gly Ser Gln Gln Leu Ala Tyr Pro Asn Lys
        35                  40                  45

Ile Ile Leu His Glu Thr Ala Asn Pro Arg Ala Thr Gly Arg Asn Glu
        50                  55                  60

Ala Thr Tyr Met Lys Asn Asn Trp Phe Asn Ala His Thr Thr Ala Ile
65                  70                  75                  80

Val Gly Asp Gly Gly Ile Val Tyr Lys Val Ala Pro Glu Gly Asn Val
                85                  90                  95

Ser Trp Gly Ala Gly Asn Ala Asn Pro Tyr Ala Pro Val Gln Ile Glu
                100                 105                 110

Leu Gln His Thr Asn Asp Pro Glu Leu Phe Lys Ala Asn Tyr Lys Ala
        115                 120                 125

Tyr Val Asp Tyr Thr Arg Asp Met Gly Lys Lys Phe Gly Ile Pro Met
        130                 135                 140

Thr Leu Asp Gln Gly Gly Ser Leu Trp Glu Lys Gly Val Val Ser His
145                 150                 155                 160

Gln Trp Val Thr Asp Phe Val Trp Gly Asp His Thr Asp Pro Tyr Gly
                165                 170                 175

Tyr Leu Ala Lys Met Gly Ile Ser Lys Ala Gln Leu Ala His Asp Leu
                180                 185                 190

Ala Asn Gly Val Ser Gly Asn Thr Ala Thr Pro Thr Pro Lys Pro Asp
        195                 200                 205

Lys Pro Lys Pro Thr Gln Pro Ser Lys Pro Ser Asn Lys Lys Arg Phe
        210                 215                 220

Asn Tyr Arg Val Asp Gly Leu Glu Tyr Val Asn Gly Met Trp Gln Ile
225                 230                 235                 240

Tyr Asn Glu His Leu Gly Lys Ile Asp Phe Asn Trp Thr Glu Asn Gly
                245                 250                 255

Ile Pro Val Glu Val Val Asp Lys Val Asn Pro Ala Thr Gly Gln Pro
                260                 265                 270

Thr Lys Asp Gln Val Leu Lys Val Gly Asp Tyr Phe Asn Phe Gln Glu
        275                 280                 285

Asn Ser Thr Gly Val Val Gln Glu Gln Thr Pro Tyr Met Gly Tyr Thr
        290                 295                 300

Leu Ser His Val Gln Leu Pro Asn Glu Phe Ile Trp Leu Phe Thr Asp
305                 310                 315                 320

Ser Lys Gln Ala Leu Met Tyr Gln
                325
```

```
<210> SEQ ID NO 33
<211> LENGTH: 289
<212> TYPE: PRT
<213> ORGANISM: Enterobacteria phage jEF24C

<400> SEQUENCE: 33

Met Ala Gly Glu Val Phe Ser Ser Leu Ile Thr Ser Val Asn Pro Asn
1               5                   10                  15

Pro Met Asn Ala Gly Ser Arg Asn Gly Ile Pro Ile Asp Thr Ile Ile
                20                  25                  30

Leu His His Asn Ala Thr Thr Asn Lys Asp Val Ala Met Asn Thr Trp
        35                  40                  45

Leu Leu Gly Gly Gly Ala Gly Thr Ser Ala His Tyr Glu Cys Thr Pro
        50                  55                  60

Thr Glu Ile Ile Gly Cys Val Gly Glu Gln Tyr Ser Ala Phe His Ala
```

```
65                   70                   75                   80

Gly Gly Thr Gly Gly Ile Asp Val Pro Lys Ile Ala Asn Pro Asn Gln
                    85                  90                  95

Arg Ser Ile Gly Ile Glu Asn Val Asn Ser Ser Gly Ala Pro Asn Trp
                100                 105                 110

Ser Val Asp Pro Arg Thr Ile Thr Asn Cys Ala Arg Leu Val Ala Asp
                115                 120                 125

Ile Cys Thr Arg Tyr Gly Ile Pro Cys Asp Arg Gln His Val Leu Gly
            130                 135                 140

His Asn Glu Val Thr Ala Thr Ala Cys Pro Gly Gly Met Asp Val Asp
145                 150                 155                 160

Glu Val Val Arg Gln Ala Gln Gln Phe Met Ala Gly Gly Ser Asn Asn
                165                 170                 175

Ala Val Lys Pro Glu Pro Ser Lys Pro Thr Pro Ser Lys Pro Ser Asn
                180                 185                 190

Asn Lys Asn Lys Glu Gly Val Ala Thr Met Tyr Cys Leu Tyr Glu Arg
                195                 200                 205

Pro Ile Asn Ser Lys Thr Gly Val Leu Glu Trp Asn Gly Asp Ala Trp
            210                 215                 220

Thr Val Met Phe Cys Asn Gly Val Asn Cys Arg Arg Val Ser His Pro
225                 230                 235                 240

Asp Glu Met Lys Val Ile Glu Asp Ile Tyr Arg Lys Asn Asn Gly Lys
                245                 250                 255

Asp Ile Pro Phe Tyr Ser Gln Lys Glu Trp Asn Lys Asn Ala Pro Trp
                260                 265                 270

Tyr Asn Arg Leu Glu Thr Val Cys Pro Val Val Gly Ile Thr Lys Lys
            275                 280                 285

Ser
```

<210> SEQ ID NO 34
<211> LENGTH: 237
<212> TYPE: PRT
<213> ORGANISM: Enterobacteria phage F168/08

<400> SEQUENCE: 34

```
Met Val Lys Leu Asn Asp Val Leu Ser Tyr Val Asn Gly Leu Val Gly
1               5                   10                  15

Lys Gly Val Asp Ala Asp Gly Trp Tyr Gly Thr Gln Cys Met Asp Leu
                20                  25                  30

Thr Val Asp Val Met Gln Arg Phe Phe Gly Trp Arg Pro Tyr Gly Asn
            35                  40                  45

Ala Ile Ala Leu Val Asp Gln Pro Ile Pro Ala Gly Phe Gln Arg Ile
        50                  55                  60

Arg Thr Thr Ser Ser Thr Gln Ile Lys Ala Gly Asp Val Met Ile Trp
65                  70                  75                  80

Gly Leu Gly Tyr Tyr Ala Gln Tyr Gly His Thr His Ile Ala Thr Glu
                85                  90                  95

Asp Gly Arg Ala Asp Gly Thr Phe Val Ser Val Asp Gln Asn Trp Ile
                100                 105                 110

Asn Pro Ser Leu Glu Val Gly Ser Pro Ala Ala Ala Ile His His Asn
                115                 120                 125

Met Asp Gly Val Trp Gly Val Ile Arg Pro Pro Tyr Glu Ala Glu Ser
            130                 135                 140

Lys Pro Lys Pro Pro Ala Pro Lys Pro Asp Lys Pro Asn Leu Gly Gln
```

```
145                150                155                160

Phe Lys Gly Asp Asp Asp Ile Met Phe Ile Tyr Tyr Lys Lys Thr Lys
                165                170                175

Gln Gly Ser Thr Glu Gln Trp Phe Val Ile Gly Gly Lys Arg Ile Tyr
            180                185                190

Leu Pro Thr Met Thr Tyr Val Asn Glu Ala Asn Asp Leu Ile Lys Arg
        195                200                205

Tyr Gly Gly Asn Thr Asn Val Thr Thr Tyr Asn Tyr Asp Asn Phe Gly
    210                215                220

Leu Ala Met Met Glu Lys Ala Tyr Pro Gln Val Lys Leu
225                230                235

<210> SEQ ID NO 35
<211> LENGTH: 25
<212> TYPE: PRT
<213> ORGANISM: Lactobacillus plantarum

<400> SEQUENCE: 35

Gly Ala Trp Lys Asn Phe Trp Ser Ser Leu Arg Lys Gly Phe Tyr Asp
1                5                10                15

Gly Glu Ala Gly Arg Ala Ile Arg Arg
            20                25

<210> SEQ ID NO 36
<211> LENGTH: 32
<212> TYPE: PRT
<213> ORGANISM: Lactobacillus plantarum

<400> SEQUENCE: 36

Arg Arg Ser Arg Lys Asn Gly Ile Gly Tyr Ala Ile Gly Tyr Ala Phe
1                5                10                15

Gly Ala Val Glu Arg Ala Val Leu Gly Gly Ser Arg Asp Tyr Asn Lys
            20                25                30

<210> SEQ ID NO 37
<211> LENGTH: 33
<212> TYPE: PRT
<213> ORGANISM: Lactobacillus plantarum

<400> SEQUENCE: 37

Phe Asn Arg Gly Gly Tyr Asn Phe Gly Lys Ser Val Arg His Val Val
1                5                10                15

Asp Ala Ile Gly Ser Val Ala Gly Ile Arg Gly Ile Leu Lys Ser Ile
            20                25                30

Arg

<210> SEQ ID NO 38
<211> LENGTH: 34
<212> TYPE: PRT
<213> ORGANISM: Lactobacillus plantarum

<400> SEQUENCE: 38

Val Phe His Ala Tyr Ser Ala Arg Gly Val Arg Asn Asn Tyr Lys Ser
1                5                10                15

Ala Val Gly Pro Ala Asp Trp Val Ile Ser Ala Val Arg Gly Phe Ile
            20                25                30

His Gly

<210> SEQ ID NO 39
```

-continued

```
<211> LENGTH: 75
<212> TYPE: PRT
<213> ORGANISM: Escherichia coli

<400> SEQUENCE: 39

Ala Gly Asp Pro Leu Ala Asp Pro Asn Ser Gln Ile Val Arg Gln Ile
1               5                   10                  15

Met Ser Asn Ala Ala Trp Gly Ala Ala Phe Gly Ala Arg Gly Gly Leu
            20                  25                  30

Gly Gly Met Ala Val Gly Ala Ala Gly Gly Val Thr Gln Thr Val Leu
        35                  40                  45

Gln Gly Ala Ala Ala His Met Pro Val Asn Val Pro Ile Pro Lys Val
    50                  55                  60

Pro Met Gly Pro Ser Trp Asn Gly Ser Lys Gly
65                  70                  75

<210> SEQ ID NO 40
<211> LENGTH: 80
<212> TYPE: PRT
<213> ORGANISM: Escherichia coli

<400> SEQUENCE: 40

Gly Asp Val Asn Trp Val Asp Val Gly Lys Thr Val Ala Thr Asn Gly
1               5                   10                  15

Ala Gly Val Ile Gly Gly Ala Phe Gly Ala Gly Leu Cys Gly Pro Val
            20                  25                  30

Cys Ala Gly Ala Phe Ala Val Gly Ser Ser Ala Ala Val Ala Ala Leu
        35                  40                  45

Tyr Asp Ala Ala Gly Asn Ser Asn Ser Ala Lys Gln Lys Pro Glu Gly
    50                  55                  60

Leu Pro Pro Glu Ala Trp Asn Tyr Ala Glu Gly Arg Met Cys Asn Trp
65                  70                  75                  80

<210> SEQ ID NO 41
<211> LENGTH: 40
<212> TYPE: PRT
<213> ORGANISM: Pseudoplectania nigrella

<400> SEQUENCE: 41

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```

COMBINATIONS OF ENGINEERED ANTIMICROBIAL PROBIOTICS FOR TREATMENT OF GASTROINTESTINAL TRACT PATHOGENS

This application is being filed as a PCT International Patent application on Dec. 23, 2019, in the name of General Probiotics, Inc., a U.S. national corporation, applicant for the designation of all countries, and Yiannis John Kaznessis, a U.S. Citizen, and Kathryn Gayle Kruziki, a U.S. Citizen, and Dimitrios Nikolaos Sidiropoulos, a U.S. Citizen, inventors for the designation of all countries, and claims priority to U.S. Provisional Patent Application No. 62/785,954, filed Dec. 28, 2018, the contents of which are herein incorporated by reference in its entirety.

REFERENCE TO SEQUENCE LISTING

This application is being filed electronically via EFS-Web and includes an electronically submitted sequence listing in .txt format. The .txt file contains a sequence listing titled "2019_12_23_269_0001WOUI_Sequence_Listing_ST25.txt" created on Dec. 23, 2019, and having a size of 32 KB. The sequence listing contained in this .txt file is part of the specification and is incorporated herein by reference in its entirety.

FIELD

Embodiments herein relate to mixtures of engineered antimicrobial probiotics for the treatment of gastrointestinal tract pathogens. More specifically, embodiments herein relate to the use of combinations of engineered antimicrobial probiotics, which have distinctly different colonization profiles, and which are genetically engineered to carry synthetic DNA constructs with distinctly different promoters, with distinctly different antimicrobial peptides and with distinctly different protein-secretion genes, for the treatment of gastrointestinal tract pathogens.

BACKGROUND

Foodborne gastrointestinal infections exact a vast toll on humans. The most common cause of death from diarrheal disease globally is non-typhoidal, foodborne and waterborne *Salmonella*. In the US, *Salmonella enterica* serotypes *Typhimurium* and *Enteritidis* are leading cause of foodborne disease outbreaks, with over 1 million infections annually, and calculated health care and lost productivity costs exceeding $3 billion. Other species, such as *Campylobacter* species, *Escherichia* species, and *Listeria* species are also foodborne infecting millions every year.

Of growing concern is the continuing emergence of microbial resistance to first line antibiotics. Over 1 million people are sickened in the U.S. by multidrug-resistant infections and over 30,000 die every year. The trends of increasingly frequent multidrug-resistant pathogens are disconcerting. In January 2017, the CDC announced the death of a woman in Nevada by a pneumonia bacterial strain that is pan-resistant, i.e. resistant to all antibiotics available in the US.

Numerous cases have been reported of antibiotic-resistant foodborne pathogens, including *Salmonella* spp. For example, in 2006, the CDC detected clusters of human infection by multi-drug resistant *Salmonella enterica* serotype Newport. This serotype is the third most common one in the US, and it is resistant to ampicillin, cephalothin, cefoxitin, amoxicillin, ceftriaxone, chloramphenicol, tetracycline, and streptomycin, among other first-line antibiotics. The CDC designated non-typhoidal *Salmonella* as a "Serious Threat" in the report "Antibiotic resistance threats in the United States, 2013".

One significant source of drug-resistance emergence is the widespread use of antibiotics in farm animal production. An estimated 14,000 tons of antibiotics, or approximately 70% of all antibiotics produced in the United States, were administered to cattle, pigs and poultry in 2015.

For decades, antibiotics have helped producers to raise healthy livestock. Antibiotics are also often used to promote growth and improve feed efficiency, even in the absence of infection. Arguably, antibiotics have facilitated and sustained (along with major advances in animal breeding and in production processes) significant livestock productivity increases.

The problem of resistance may be exacerbated from the unregulated use of antibiotics in agriculture. An estimated 97% of antibiotics administered in livestock were over-the-counter, often used as growth promoters in 2014. This sub-therapeutic administration of antibiotics to animals likely creates a vast reservoir for the selection of drug-resistant bacteria that can infect humans through food.

Alarmingly, there is substantial overlap between classes of antibiotics listed as critically important for human health by the World Health Organization and those antibiotics listed as critically important in agriculture by the World Organization for Animal Health. For example, three classes of antibiotics, quinolones, 3rd and 4th generation cephalosporins, and macrolides are reportedly used in agriculture, even though they are among the few viable therapeutic solutions against certain serious infections in humans.

The precise contribution of antibiotics used in livestock to human infections by antibiotic-resistant microbes is under debate. In complex systems such as food production, it is indeed difficult to establish causal relationships between the use of antibiotics in animal feed and gastrointestinal infections where antibiotic-resistant microbes affect human populations. Nevertheless, there is undisputed evidence that transmission of resistant strains to humans does occur through food.

Because of these concerns, the European Union banned the use of antibiotics in food animal production in 2006. In the United States, the FDA also moved to curtail the use of medically important antibiotics for livestock production purposes. Drug companies have voluntarily adopted FDA Guidance #209 and Guidance #213, revising the FDA-approved labeled use conditions to remove the use of over-the-counter antimicrobial drugs for production purposes. The intent is to change the marketing status from over-the-counter to Veterinary Feed Directive (VFD) for antibiotics administered to animals.

From the FDA's Strategy on Antimicrobial Resistance website: "All 25 affected animal drug companies agreed to work with FDA to remove production uses for growth promotion and feed efficiency from the approved uses of their drug products and move the therapeutic uses of these products from over-the-counter availability to a marketing status requiring veterinary oversight. By December 2016, we expect to see significant changes in the way medically important antibiotics are used in animal agriculture as compared to how they have been used for decades".

Beginning in 2017, over-the-counter antibiotics ceased being used in animal production. Antibiotics are now only prescribed for sick animals by licensed veterinarians. This is arguably a step in the right direction, ensuring judicious use of antibiotics and curbing the pace of resistance emergence.

However, major foodborne pathogens like *Salmonella* or *Campylobacter* do not typically sicken animals. It is perhaps then not unreasonably speculative to suggest that because of the effective ban of antibiotics used preventatively, and because of the ease of bacteria to spread in animals, there will be higher carriage of foodborne pathogens in live animals and, consequently, a higher frequency of contaminated food produced and delivered to consumers.

SUMMARY

Embodiments herein relate to engineered antimicrobial probiotics for the treatment of gastrointestinal tract pathogens. In an embodiment, a composition for treatment of an animal is included. The composition can include a first genetically engineered bacterium comprising a first exogenous polynucleotide. The first exogenous polynucleotide can include a first heterologous promoter and a first polynucleotide that encodes a first antimicrobial protein, wherein the first polynucleotide is operably linked to the first heterologous promoter. The composition can also include a second genetically engineered bacterium comprising a second exogenous polynucleotide. The second exogenous polynucleotide can include a second heterologous promoter and a second polynucleotide that encodes a second antimicrobial protein, wherein the second polynucleotide is operably linked to the second heterologous promoter. The first heterologous promoter can be directly or indirectly induced by one set of exogenous environmental conditions found in the gastrointestinal tract of the animal. The second heterologous promoter can be directly or indirectly induced by a second set of exogenous environmental conditions found in the gastrointestinal tract of the animal.

In an embodiment, a method for treating a disease associated with the accumulation of a pathogenic bacterium is included. The method can include administering to an animal in need thereof, a composition. The composition can include a first genetically engineered bacterium comprising a first exogenous polynucleotide. The first exogenous polynucleotide can include a first heterologous promoter and a first polynucleotide that encodes a first antimicrobial protein, wherein the first polynucleotide is operably linked to the first heterologous promoter. The composition can also include a second genetically engineered bacterium comprising a second exogenous polynucleotide. The second exogenous polynucleotide can include a second heterologous promoter and a second polynucleotide that encodes a second antimicrobial protein, wherein the second polynucleotide is operably linked to the second heterologous promoter. The first heterologous promoter can be directly or indirectly induced by one set of exogenous environmental conditions found in the gastrointestinal tract of the animal. The second heterologous promoter can be directly or indirectly induced by a second set of exogenous environmental conditions found in the gastrointestinal tract of the animal.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 12 is a table showing microenvironments within the digestive tract of poultry.

Figure 1:
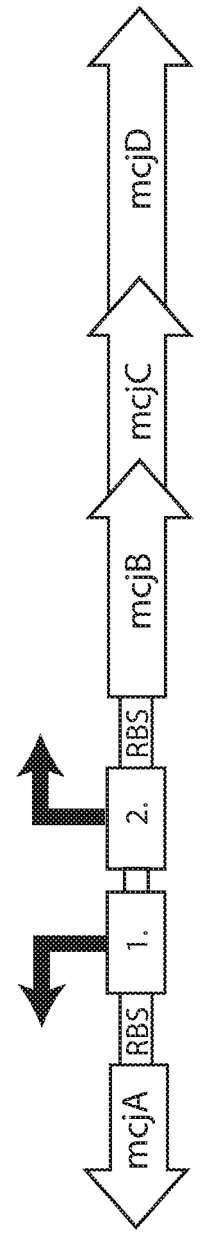
FIG. 1 is a schematic diagram of the native MJ25 production system. In the native production system promoters for mcjA and mcjBCD are dependent on a low nutrient environment, making this an unreliable peptide production system.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

There is a significant, pressing need to develop and test new antimicrobial technologies in order to eliminate pathogens in animals, to curtail the use of antibiotics in agriculture, to limit losses during production and to lower the risk of human disease caused by foodborne pathogens.

In accordance with various embodiments herein, compositions are included for treatment of an animal that can reduce or eliminate pathogens in animals allowing for a reduction in or the elimination of the use of antibiotics.

In various embodiments, a composition is included with a first genetically engineered bacterium comprising an exogenous polynucleotide. The exogenous polynucleotide of the first genetically engineered bacterium includes a first heterologous promoter controlling expression of a first polynucleotide that encodes a first antimicrobial protein. The composition also includes a second genetically engineered bacterium comprising an exogenous polynucleotide. The exogenous polynucleotide of the second genetically engineered bacterium includes a second heterologous promoter controlling expression of a second polynucleotide that encodes a second antimicrobial protein. The first and second antimicrobial peptides can be the same or different. The first and second genetically engineered bacteria can be the same strain or they can be different.

In various embodiments, the first heterologous promoter is directly or indirectly induced by one set of exogenous environmental conditions found in the gastrointestinal tract of the animal and the second heterologous promoter is directly or indirectly induced by a second set of exogenous environmental conditions found in the gastrointestinal tract of the animal. In this manner, levels of expression of the first antimicrobial protein relative to levels of expression of the second antimicrobial protein can vary throughout the gastrointestinal tract of the animal, with expression of one being greater at one or more regions and expression of the other being greater at one or more distinct regions. This tuned expression pattern can allow for more effective control of pathogens in the gastrointestinal tract of the animal.

In various embodiments, the antimicrobial activity of the first antimicrobial peptide is directly or indirectly dependent on one set of exogenous environmental conditions found in the gastrointestinal tract of the animal and the antimicrobial activity of the second antimicrobial peptide is directly or indirectly dependent by a second set of exogenous environmental conditions found in the gastrointestinal tract of the animal. In this manner, the activity of the first antimicrobial protein relative to the activity of the second antimicrobial protein can vary throughout the gastrointestinal tract of the animal, with activity against a pathogen of one peptide being greater at one or more regions and activity against the same pathogen of the other peptide being greater at one or more distinct regions. This tuned activity pattern can allow for more effective control of pathogens in the gastrointestinal tract of the animal.

In various embodiments, the colonization profile of the first genetically engineered bacterium is directly or indirectly dependent on one set of exogenous environmental conditions found in the gastrointestinal tract of the animal and the colonization profile of the second genetically engineered bacterium is directly or indirectly dependent on a second set of exogenous environmental conditions found in the gastrointestinal tract of the animal. In this manner, levels of colonization of the genetically engineered bacterium relative to levels of colonization of the second engineered bacterium can vary throughout the gastrointestinal tract of the animal, with colonization of one bacterium being greater at one or more regions and colonization of the other bacterium being greater at one or more distinct regions. This tuned colonization pattern can allow for more effective control of pathogens in the gastrointestinal tract of the animal.

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (e.g., dimers, trimers, tetramers). Thus, the terms peptide, oligopeptide, enzyme, subunit, and protein are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region," "coding sequence," and "open reading frame" are used interchangeably and refer to a nucleotide sequence that encodes a protein and, when placed under the control of appropriate regulatory sequences expresses the encoded protein. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

As used herein, a "polycistronic mRNA" refers to a transcription product that includes two or more coding regions. Expression of the two or more coding regions is controlled by a single promoter, and the series of the two or more coding regions that are transcribed to produce a polycistronic mRNA is referred to as an operon.

As used herein, "genetically modified bacterium" refers to a bacterium which has been altered "by the hand of man." A genetically modified bacterium includes a bacterium into which has been introduced an exogenous polynucleotide, e.g., an expression vector.

As used herein, a "vector" is a replicating polynucleotide, such as a plasmid, to which another polynucleotide may be attached so as to bring about the replication of the attached polynucleotide.

As used herein, an "exogenous protein" and "exogenous polynucleotide" refers to a protein and polynucleotide, respectively, which is not normally or naturally found in a microbe, and/or has been introduced into a microbe. An exogenous polynucleotide may be separate from the genomic DNA of a cell (e.g., it may be a vector, such as a plasmid), or an exogenous polynucleotide may be integrated into the genomic DNA of a cell.

As used herein, a "heterologous" polynucleotide, such as a heterologous promoter, refers to a polynucleotide that is not normally or naturally found in nature operably linked to another polynucleotide, such as a coding region. As used herein, a "heterologous" protein or "heterologous" amino acids refers to amino acids that are not normally or naturally found in nature flanking an amino acid sequence.

As used herein, the term "variant" refers to a polypeptide that comprises one or more differences in the amino acid sequence of the variant relative to a reference sequence. For example, a "variant" polypeptide may include one or more deletions, additions or substitutions relative to a reference sequence. The term "variant" is not intended to limit the variant polypeptide to only those polypeptides made by the modification of an existing polypeptide or nucleic acid molecule encoding the reference sequence, but may include variant polypeptides that are made de novo or starting from a polypeptide other than the reference sequence.

As used herein, the term "conservative variant" shall refer to sequences which reflect the incorporation of conservative amino acid substitutions. Conservative substitution tables are well known in the art (see for example Creighton (1984) Proteins. W. H. Freeman and Company (Eds) and Table 1 below).

TABLE 1

Examples of Conservative Amino Acid Substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein. A candidate protein is the protein being compared to the reference protein. A candidate protein may be isolated, for example, from a microbe, or can be produced using recombinant techniques, or chemically or enzymatically synthesized.

Unless modified as otherwise described herein, a pairwise comparison analysis of amino acid sequences can be carried out using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on. Alternatively, polypeptides may be compared using the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions.

Thus, as used herein, a candidate protein useful in the methods and compositions described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence.

Alternatively, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

Conditions that are "suitable" for an event to occur, such as expression of an exogenous polynucleotide in a cell to produce a protein, or production of a product, or "suitable" conditions are conditions that do not prevent such events from occurring. Thus, these conditions permit, enhance, facilitate, and/or are conducive to the event.

As used herein, an "animal" includes members of the class Mammalia and members of the class Ayes, such as human, avian, bovine, caprine, ovine, porcine, equine, canine, and feline.

As used herein, the recitations of numerical ranges by endpoints include all numbers subsumed within that range (e.g., 1 to 5 includes 1, 1.5, 2, 2.75, 3, 3.80, 4, 5, etc.).

As used herein, "combination" of engineered antimicrobial probiotics means a set of two or more distinctly different microorganisms that may vary in their species identity, or in their strain identity, or in the synthetic DNA sequences they are engineered with, including in the DNA promoters, antimicrobial peptides, and secretion genes encoded in the synthetic DNA sequence.

For any method disclosed herein that includes discrete steps, the steps may be conducted in any feasible order. And, as appropriate, any combination of two or more steps may be conducted simultaneously.

Environmental Variations in the Digestive Tract

The GI tract is a vastly complex environment with varying chemical composition, nutrient availability, containing an immensely complex ecology of microorganisms. Thus, it is important to understand how microbes in general, and probiotics in particular, colonize the GI tract environment. This understanding informs the choice of probiotic organisms and can be used for consistent, strong colonization of probiotics for consistent elimination of pathogens.

It is also important to understand how microbes in general, and probiotics in particular, respond to the GI tract environment and how these responses modulate gene expression. This understanding informs the design of DNA promoters that can be used for consistent, strong expression of antimicrobial peptides for consistent elimination of pathogens.

It is also important to understand how antimicrobial peptides structurally fold and are functionally active against pathogens in the GI tract environment. This understanding informs the choice of antimicrobial peptides and can be used for consistent, strong activity for consistent elimination of pathogens.

The digestive tract of poultry has a wide range of microenvironments which vary from one another in terms of pH, nutrient content, microbiome, bile concentration, immunogenicity, and oxygen availability. For example, pH varies from 2.5 in the proventriculus to 8 in the colon. This means that depending on the site of infection, a probiotic should be designed to survive in the pH of that site as well as in any other pH fluctuations it might face until it reaches the site of infection. Furthermore, availability of nutrients also varies quite extensively in the GI tract, especially after the duodenum and jejunum where most of nutrient absorption has already occurred. Besides nutrient variation caused by abortion, the gut microbiome can vary between poultry which can also impact the survival rate of a probiotic in the gut. In addition, another important component is oxygen availability which also varies along the path of the GI tract. FIG. 12 herein shows conditions at various points in the intestinal tract of poultry.

The presence of these distinct microenvironments offers an opportunity to precisely engineer probiotics to deliver selected AMPs at targeted sites to enhance the reduction and/or elimination of pathogens.

Probiotics

The Food and Agriculture Organization of the United Nations (FAO) defines probiotics as "live microorganisms that, when administered in adequate amounts, confer a health benefit on the host." A plethora of microbes are considered probiotics and can be used in an engineered state in accordance with embodiments herein, including lactobacilli, bifidobacteria, bacilli and enterococci.

Examples of probiotics are shown in TABLE 2.

TABLE 2

| Example probiotic organisms. | | |
|---|---|---|
| Species | Strain | References |
| Bacillus subtilis | 588, CA #20, DSM 17299, PB6, ATCC-PTA 6737, DSM 5750 | Alexopoulos et al., 2004a; Davis et al., 2008; Rahman et al., 2013; Afsharmanesh and Sadaghi, 2014 |
| Bifidobacterium thermophilus | | Khaksar, Golian and Kermanshahi, 2012; Pedroso et al., 2013 |
| Escherichia coli | Nissle 1917 (DSM 6601), Symbioflor (DSM 17257) genotypes G1/2 (DSM 16441), G3/10 (DSM 16443), G4/9, and G5 | Hashemzadeh et al., 2013 |
| Enterococcus faecium | 589, NCIMB 11181, E1708, DSM 10663, | Mountzouris et al., 2010; Giannenas et al., 2012; Khaksar, Golian and Kermanshahi, 2012; Wideman et al., 2012; Seo et al., 2010 |
| Enterococcus faecalis | — | |
| Lactobacillus acidophilus | | Morishita et al., 1997; Haghighi et al., 2008; Daskiran et al., 2012; Khaksar, Golian and Kermanshahi, 2012; Shim et al., 2012; Rahman et al., 2013; Zhang et al., 2014a |
| Lactobacillus plantarum | — | Daskiran et al., 2012; Rahman et al., 2013 |
| Lactobacillus brevis | I 12, I 211, I 218, I 23, I 25 | Mookiah et al., 2014 |
| Lactobacillus casei | CECT 4043 | Fajardo et al., 2012; Khaksar, Golian and Kermanshahi, 2012; Landy and Kavyani, 2013 |

TABLE 2-continued

Example probiotic organisms.

| Species | Strain | References |
|---|---|---|
| Lactobacillus delbrueckii, | — | Daskiran et al., 2012 |
| Lactobacillus reuteri | 514, C 1, C10, C16, DSM 16350, DSM 16350 | Mountzouris et al., 2010; Giannenas et al., 2012; Wideman et al., 2012; Mookiah et al., 2014 |
| Lactobacillus gallinarum | I 16, I 26, LCB 12 | Ohya, Marubashi and Ito, 2000; Mookiah et al., 2014 |
| Lactococcus lactis | CECT 539 | Fajardo et al., 2012 |

An official list of microbes that can be marketed as generally regarded as safe (GRAS) direct-fed microbials (DFMs) is compiled by the Association of American Feed Control Officials (AAFCO). These DFMs are considered either as fermentation products or yeast products and are accepted by the FDA as safe. Embodiments herein can include engineered versions of any direct-fed microbial that is GRAS.

Competitive exclusion has been long believed to be an important mechanism of action, with naturally occurring probiotic organisms colonizing the gut and inhibiting pathogens from taking hold. Inhibition may occur simply as a result of limited resources, or more actively by the expression and secretion of inhibiting substances.

In accordance with embodiments herein, probiotic bacteria are modified using synthetic biology techniques to express and deliver antimicrobial proteins/peptides (including, but not limited to, bacteriocins) in the gastrointestinal tract of animals. Probiotics are promising therapeutic delivery vehicles: they are bile-resistant, they are generally regarded as safe to consume, and they may reside inside GI tracts for tunable time intervals. Survival during passage through the esophagus and stomach is a critical attribute of probiotic organisms. Probiotics can survive the gastrointestinal environment and can withstand low pH and high concentration of bile salts. Probiotics can reach and often colonize the GI tract of animals. The GI tract is the major reservoir of pathogens, and probiotics can be acting at the site of infection.

In accordance with embodiments herein, compositions are included comprising of a combination of different, distinct probiotic bacterial species. Because of the variations in physical and chemical properties in the different compartments of the gastrointestinal tract, specific probiotics colonize and persist in the stomach, small intestine, and large intestine at varying levels of population density. For example, Lactobacillus acidophilus preferentially colonizes the duodenum whereas E. coli preferentially colonizes the large intestine. For example, Lactobacillus reuteri induces significant colonization of the upper GI tract, specifically the stomach, duodenum, and ileum (Valeur, Nana et al. "Colonization and immunomodulation by Lactobacillus reuteri ATCC 55730 in the human gastrointestinal tract" Applied and environmental microbiology vol. 70, 2 (2004): 1176-81). Escherichia coli Nissle on the other hand is typically found in the lower GI tract, particularly in the colon as well as the lower parts of the small intestine (Trudy M. Wassenaar (2016). Insights from 100 Years of Research with Probiotic E. Coli. European journal of microbiology & immunology, 6(3), 147-161. doi:10.1556/1886.2016.00029). A combination of these two bacterial species can allow for more effective control of pathogens in the gastrointestinal tract of animals or humans.

Although pathogens can be found throughout the GI tract, they also preferentially adhere to different parts of the GI tract. Salmonella spp. for example preferentially colonizes ceca, whereas Streptococcus faecium colonize the small intestine (Fuller, Rozlyn & B Houghton, S & E Brooker, B. (1981). Attachment of Streptococcus faecium to the Duodenal Epithelium of the Chicken and Its Importance in Colonization of the Small Intestine. Applied and environmental microbiology. 41. 1433-41). As such, probiotic mixtures are particularly important in order to cover not only domains in which a pathogen of interest preferentially colonize, but also as it passes through the GI tract to its primary site of colonization. This allows us to target the pathogen both at the primary site of colonization, upstream and downstream of that site.

Different strains, even ones belonging to the same bacterial species, often exhibit different survival and colonization profiles across different animals. For example, a probiotic isolated from the intestinal tract of humans may be better adapted to this environment compared to a soil bacterial isolate. Different strains can also exhibit different expression profiles from the same genetic construct under different environmental conditions. A combination of bacterial strains with various colonization and persistence profiles can allow for more effective control of pathogens in the gastrointestinal tract of animals or humans.

Antimicrobial Peptides Antimicrobial peptides are small proteins, typically between 10 and 100 amino acids in length that inhibit, and often kill, certain bacteria. As such, an antimicrobial peptide has antimicrobial activity that inhibits or kills a target microbe. The target microbe may be a Gram negative such as E. coli or a member of the genus Salmonella. Examples of Salmonella include, for instance, Salmonella enterica serotypes Typhimurium, Enteritidis, Gallinarum, Pullorum, Saintpaul, Kentucky, Indiana, Hadar and Heidelberg. Examples of E. coli include, for instance, strains O157:H7, O104:H4, O121, O26, O103, O111, O145, and O104:H21. The target microbe may be a Gram positive such as a member of the genus Enterococcus. Examples of Enterococcus spp. include, for instance, E. faecium and E. faecalis. The target microbe may be in vitro or in vivo. For instance, in one embodiment, a target microbe may be one that is present in the gastrointestinal tract or urogenital system of a subject, and optionally may be pathogenic to the subject. For instance, in another embodiment, a target microbe may be one that is present in the ovaries of hens, contaminating the eggs inside the chicken before the shells are formed.

Whether an antimicrobial peptide has antimicrobial activity can be determined using different indicator strains. Examples of indicator strains include, but are not limited to, pathogenic Salmonella, enterohemorrhagic E. coli O157:H7, lactic acid bacteria such as Lactococcus lactis, Lactobacillus acidophilus, Lb. reuteri, Lb. sakei and Lb. bulgaricus, and Enterococcus spp. Examples of suitable indicator strains include, but are not limited to, those listed in TABLE 3 below. In one embodiment, an indicator strain is a member of the genus Enterococcus, such as E. faecalis and E. faecium. Methods for testing the activity of an antimicrobial peptide include, but are not limited to, the stab-on-agar test as well as other methods useful for evaluating the activity of bacteriocins. Such methods are known in the art and are routine.

TABLE 3

| Examples of indicator strains. |
| --- |
| *Escherichia coli* serotype O157:H7 |
| *Salmonella enterica* subsp *enterica* |
| serovar *Typhimurium* |
| serovar Tennessee |
| serovar St. Paul |
| serovar *Infantis* |
| *Lactococcus lactis* subsp *lactis* IL1403 |
| *Lactobacillus acidophilus* ATCC 4356 |
| *Lactobacillus bulgaricus* ATCC 11842 |

TABLE 3-continued

| Examples of indicator strains. |
| --- |
| *Enterococcus faecalis* ATCC 700802 |
| *Enterococcus faecalis* ATCC 47077 |

An antimicrobial peptide may be naturally occurring or may be engineered. Antimicrobial peptides are produced by all classes of organisms, including mammals, bacteria, and phage. Examples of antimicrobial peptides are shown in TABLE 4.

TABLE 4

Exemplary antimicrobial peptides

| Antimicrobial Peptide | Amino Acid Sequence | Origin |
| --- | --- | --- |
| Microcin J25 | GGAGHVPEYFVGIGTPISFYG (SEQ ID NO: 13) | *E. coli* (18) |
| Enterocin A (EntA) | TTHSGKYYGNGVYCTKNKCTV DWAKATTCIAGMSIGGFLGGAIP GKC (SEQ ID NO: 14) | *E. faecium* (1) |
| Enterocin P (EntP) | ATRSYGNGVYCNNSKCWVNWG EAKENIAGIVISGWASGLAGMG H (SEQ ID NO: 15) | *E. faecium* (2) |
| Enterocin B | ENDHRMPNELNRPNNLSKGGAK CGAAIAGGLFGIPKGPLAWAAG LANVYSKCN (SEQ ID NO: 16) | *E. faecium* (23) |
| Hiracin JM79 (HirJM79) | ATYYGNGLYCNKEKCWVDWN QAKGEIGKIIVNGWVNHGPWAP RR (SEQ ID NO: 17) | *E. hirae* (3) |
| Protegrin 1 (PG-1) | RGGRLCYCRRRFCVCVGR (SEQ ID NO: 18) | Pig leukocyte (5) |
| PC64A | LTYCRRRFCVTV (SEQ ID NO: 19) | PG-1 analogue (6) |
| Alyteserin-1a | GLKDIFKAGLGSLVKGIAAHVA N (SEQ ID NO: 20) | Peptide from the skin of the frog Alytes obstetricans (8) |
| Fowlicidin | RVKRVWPLVIRTVIAGYNLYRAI KKK (SEQ ID NO: 21) | Cathelicidin from chicken (9) |
| Microcin 24 | AGDPLADPNSQIVRQIMSNAAW GPPLVPERFRGMAVGAAGGVTQ TVLQGAAAHMPVNVPIPKVPMG PSWNGSKG (SEQ ID NO: 22) | *Escherichia coli* (10) |
| Colicin V (Microcin V) | ASGRDIAMAIGTLSGQFVAGGIG AAAGGVAGGAIYDYASTHKPNP AMSPSGLGGTIKQKPEGIPSEAW NYAAGRLCNWSPNNLSDVCL (SEQ ID NO: 23) | *Escherichia coli* (11) |
| Acidocin LCHV NP | NVGVLNPPPLV (SEQ ID NO: 24) | Bacteriocin from *Lb. acidophilus* n.v. Er 317/402 strain Narine (12) |
| Acidocin LCHV HV | NVGVLNPPMLV (SEQ ID NO: 25) | Bacteriocin from *Lb. acidophilus* n.v. Er 317/402 strain Narine (12) |
| Acidocin LCHV LP | NVGVLLPPPLV (SEQ ID NO: 26) | Bacteriocin from *Lb. acidophilus* n.v. Er 317/402 strain Narine (12) |
| Acidocin LCHV LM | NVGVLLPPMLV (SEQ ID NO: 27) | Bacteriocin from *Lb. acidophilus* n.v. Er 317/402 strain Narine (12) |

TABLE 4-continued

Exemplary antimicrobial peptides

| Antimicrobial Peptide | Amino Acid Sequence | Origin |
|---|---|---|
| LGG NPSRQERR | NPSRQERR (SEQ ID NO: 28) | Small bioactive peptide from *Lactobacillus* GG (12) |
| LGG PDENK | PDENK (SEQ ID NO: 29) | Small bioactive peptide from *Lactobacillus* GG (13) |
| Endolysin 170 (Lys170) | MAGEVFSSLITSVNPNPMNAGSR NGIPIDTIILHHNATTNKDVAMN TWLLGGGAGTSAHYECTPTEIIG CVGEQYSAFHAGGTGGIDVPKIA NPNQRSIGIENVNSSGAPNWSVD PRTITNCARLVADICTRYGIPCDR QHVLGHNEVTATACPGGMDVD EVVRQAQQFMAGGSNNAVKPEP SKPTPSKPSNNKNKEGVATMYC LYERPINSKTGVLEWNGDAWTV MFCNGVNCRRVSHPDEMKVIED IYRKNNGKDIPFYSQKEWNKNA PWYNRLETVCPVVGITKKS (SEQ ID NO: 30) | *E. faecalis* phage F170/08 (4) |
| Ply V12 | MSNINMETAIANMYALKARGIT YSMNYSRTGADGTGDCSGTVYD SLRKAGASDAGWVLNTDSMHS WLEKNGFKLIAQNKEWSAKRGD VVIFGKKGASGGSAGHVVIFISST QIIHCTWKSATANGVYVDNEAT TCPYSMGWYVYRLNGGSTPPKP NTKKVKVLKHATNWSPSSKGAK MASFVKGGTFEVKQQRPISYSYS NQEYLIVNKGTVLGWVLSQDIE GGYGSDRVGGSKPKLPAGFTKE EATFINGNAPITTRKNKPSLSSQT ATPLYPGQSVRYLGWKSAEGYI WIYATDGRYIPVRPVGKEAWGT FKQDIEGGYGSDRVGGSKPKLPA GFTKEEATFINGNAPITTRKNKPS LSSQTATPLYPGQSVRYLGWKS AEGYIWIYATDGRYIPVRPVGKE AWGTFK (SEQ ID NO: 31) | Encoded by phage F1 (14) |
| EFAL-1 | MKLKGILLSVVTTFGLLFGATNV QAYEVNNEFNLQPWEGSQQLAY PNKIILHETANPRATGRNEATYM KNNWFNAHTTAIVGDGGIVYKV APEGNVSWGAGNANPYAPVQIE LQHTNDPELFKANYKAYVDYTR DMGKKFGIPMTLDQGGSLWEKG VVSHQWVTDFVWGDHTDPYGY LAKMGISKAQLAHDLANGVSGN TATPTPKPDKPKPTQPSKPSNKK RFNYRVDGLEYVNGMWQIYNE HLGKIDFNWTENGIPVEVVDKV NPATGQPTKDQVLKVGDYFNFQ ENSTGVVQEQTPYMGYTLSHVQ LPNEFIWLFTDSKQALMYQ (SEQ ID NO: 32) | Produced by phage EFAP-1 (15) |
| ORF9 | MAGEVFSSLITSVNPNPMNAGSR NGIPIDTIILHHNATTNKDVAMN TWLLGGGAGTSAHYECTPTEIIG CVGEQYSAFHAGGTGGIDVPKIA NPNQRSIGIENVNSSGAPNWSVD PRTITNCARLVADICTRYGIPCDR QHVLGHNEVTATACPGGMDVD EVVRQAQQFMAGGSNNAVKPEP SKPTPSKPSNNKNKEGVATMYC LYERPINSKTGVLEWNGDAWTV MFCNGVNCRRVSHPDEMKVIED IYRKNNGKDIPFYSQKEWNKNA PWYNRLETVCPVVGITKKS (SEQ ID NO: 33) | From phage jEF24C (16) |

TABLE 4-continued

Exemplary antimicrobial peptides

| Antimicrobial Peptide | Amino Acid Sequence | Origin |
|---|---|---|
| Lys168 | MVKLNDVLSYVNGLVGKGVDA DGWYGTQCMDLTVDVMQRFFG WRPYGNAIALVDQPIPAGFQRIR TTSSTQIKAGDVMIWGLGYYAQ YGHTHIATEDGRADGTFVSVDQ NWINPSLEVGSPAAAIHHNMDG VWGVIRPPYEAESKPKPPAPKPD KPNLGQFKGDDDIMFIYYKKTK QGSTEQWFVIGGKRIYLPTMTYV NEANDLIKRYGGNTNVTTYNYD NFGLAMMEKAYPQVKL (SEQ ID NO: 34) | From phage F168/08 (17) |
| Plantaricin JK (PlnJK). Plantaricin JK is comprised of the two peptides Plantaricin J (PlnJ) and Plantaricin K (PlnK) | PlnJ GAWKNFWSSLRKGFYDGEAGR AIRR (SEQ ID NO: 35) PlnK RRSRKNGIGYAIGYAFGAVERA VLGGSRDYNK (SEQ ID NO: 36) | Class Iib heterodimeric bacteriocin produced by *Lactobacillus plantarum* C11 (19) |
| Plantaricin EF (PlnEF). Plantaricin EF is comprised of the two peptides Plantaricin E (PlnE) and Plantaricin F (PlnF) | PlnE FNRGGYNFGKSVRHVVDAIGSV AGIRGILKSIR (SEQ ID NO: 37) PlnF VFHAYSARGVRNNYKSAVGPAD WVISA VRGFIHG (SEQ ID NO: 38) | Class Iib heterodimeric bacteriocin produced by *Lactobacillus plantarum* C11 (20) |
| Microcin N | AGDPLADPNSQIVRQIMSNAAW GAAFGARGGLGGMAVGAAGGV TQTVLQGAAAHMPVNVPIPKVP MGPSWNGSKG (SEQ ID NO: 39) | Produced by *E. coli* (21) |
| Microcin L | GDVNWVDVGKTVATNGAGVIG GAFGAGLCGPVCAGAFAVGSSA AVAALYDAAGNSNSAKQKPEGL PPEAWNYAEGRMCNW (SEQ ID NO: 40) | Produced by *E. coli* (22) |
| Plectasin | GFGCNGPWDEDDMQCHNHCKSI KGYKGGYCAKGGFVCKCY (SEQ ID NO: 41) | Produced by *Pseudoplectania nigrella* (24) |

1. Aymerich et al., 1996, Appl Environ Microbiol. 62:1676-1682; 2. Cintas et al., 1997, Appl Environ Microbiol., 63:4321-4330; 3. Sánchez et al., 2007, FEMS Microbiol Lett. 270:227-236; 4. Proença et al., 2012, Microb Drug Resist., 18:322-332; 5. Fahrner et al., 1996, Chemistry & Biology 3:543-550; 6, Chang et al., U.S. Pat. No. 5,994,306; 7. Szabo et al., 2010, International journal of antimicrobial agents 35:357-361; 8. Conlon et al., 2009, Peptides 30, 1069-1073; 9. Xiao, 2005, Journal of Biological Chemistry 281:2858-2867; 10. O'Brien et al., 1994, Plasmid 31:288-296; 11. Gillor et al., 2004, Advances in applied microbiology 54:129-146; 12. Mkrtchyan et al., 2010, International journal of antimicrobial agents 35:255-260; 13. Lu et al., 2009, 1 Pediatr. Gastroenterol. Nutr. 49:23-30; 14. Yoong et al., 2004, J. Bacteriol. 186:4808-4812; 15. Uchiyama et al., 2011, Appl Environ Microbiol. 77:580-585; 16. Son et al., 2010, J. Appl Microbiol. 108:1769-1779; 17. Proença et al., 2012, Microb Drug Resist. 18:322-332; 18, Salomon and Farias, 1992, J Bacteriol. 174:7428-7435; 19: Hauge et al. 1999, J Bacteriol., 181(3):740-7; 20: Kyriakou et al., 2016, Biochim Biophys Acta. 1858(4):824-35; 21: Corsini et al., 2010, FEMS Microbiol Lett. 312(2):119-25. 22: Pons et al., 2004, Antimicrob Agents Chemother. 48(2): 505-13. 23: Casaus et al., 1997, Microbiology. 143(Pt 7):2287-94. 24: Mygind et al., 2005, Nature. 437 (7061):975-80. 25: Chen et al., 2017, AMB Express. 7(1):46.

Examples of antimicrobial peptides also include those that are essentially identical to any one of the antimicrobial peptides in TABLE 4. As used herein, in the context of a protein "essentially identical" refers to a protein that differs from one of the proteins disclosed herein. A protein that is essentially identical to an antimicrobial peptide differs from one of the antimicrobial peptides in in TABLE 4 at 1, 2, 3, 4, 5, 6, 7, 8, 9, 10, 11, or 12 amino acid residues and has antimicrobial activity. In one embodiment, the difference is a conservative substitution. Conservative amino acid substitutions are defined to result from exchange of amino acids residues from within one of the following classes of residues: Class 1: Ala, Gly, Ser, Thr, and Pro (representing small aliphatic side chains and hydroxyl group side chains); Class 2: Cys, Ser, Thr, and Tyr (representing side chains including an —OH or —SH group); Class 3: Glu, Asp, Asn, and Gln (carboxyl group containing side chains): Class 4: His, Arg, and Lys (representing basic side chains); Class 5: Ile, Val, Leu, Phe, and Met (representing hydrophobic side chains); and Class 6: Phe, Trp, Tyr, and His (representing aromatic side chains).

Bacteriocins are antimicrobial peptides (AMPs) produced by a wide range of bacteria. Unlike antibiotic peptides such as the gramicidins, polymyxins, or glycopeptides which are formed by multienzyme complexes, bacteriocins are ribosomally synthesized, i.e., their sequence is gene encoded. The exact biological role of bacteriocins is still unknown but it is believed that bacteriocins have a vital role in ecology as they influence the composition of the microbial flora in certain growth habitats, e.g., the gastrointestinal tract of humans and animals.

Numerous bacteriocins exert their antimicrobial effect by interfering with the cell membrane integrity of target bacteria, and they share several physicochemical features. They are often heat-stable, small in size, often cationic and have amphiphilic or hydrophobic structure. However, they differ greatly from eukaryotic AMPs which often serve as the first line of defense against invading pathogens in mammals: bacteriocins are very potent, acting at pico- to nanomolar concentrations, whereas micromolar concentrations are often required for the activity of eukaryotic AMPs.

Most bacteriocins also have a very narrow target spectrum; individual bacteriocins are active against a just few species or genera. On the contrary, eukaryotic AMPs as well as traditional antibiotics are generally much less specific, targeting a large diversity of different bacteria. Consequently, in terms of potency and specificity, bacteriocins may be superior to traditional antibiotics and eukaryotic AMPs.

Bacteriocins can thus be very useful in therapeutic treatments where a particular pathogen is to be removed from a complex multi-species environment (such as in the gut) without causing adverse secondary effects as normally occur with common antibiotics.

Bacteriocins include class I and class II bacteriocins. An example of class II bacteriocins includes members of the subclass IIa bacteriocins. Class IIa bacteriocins are small (usually 37 to 48 amino acid), heat-stable, and non-posttranslationally modified proteins that are typically positively charged and may contain an N-terminal consensus sequence-Tyr-Gly-Asn-Gly-(Val/Lys)-Xaa-Cys-. Examples of class IIa bacteriocins include, but are not limited to, those described in TABLE 4. Another example of class II bacteriocins includes members of the subclass IIb bacteriocins. Class IIb bacteriocins are heterodimeric bacteriocins that require two different molecules at approximately equal concentrations to exhibit optimal activity. Examples of class IIb bacteriocins include, but are not limited, to those described in TABLE 4.

Another example of antimicrobial peptides includes endolysins. Endolysins are double-stranded DNA bacteriophage-encoded peptidoglycan hydrolases produced in phage-infected bacterial cells, and cause rapid lysis when applied to Gram-positive bacteria (Fenton et al., 2010, Bioeng Bugs. 1:9-16; Fischetti, 2008, Curr Opin Microbiol. 11:393-400).

For all the promise of bacteriocins, in particular, and antimicrobial peptides, in general, a critical barrier in using these compounds as therapeutics exists. AMPs cannot be administered orally or intravenously for therapeutic purposes. As proteins they are quickly degraded, and in high initial dosages they may become toxic to host cells. However, in accordance with embodiments herein, probiotics are engineered to express and secrete AMPs directly into the gastrointestinal tract overcoming traditional challenges associated with the use of AMPs for treating various pathogens.

A nucleotide sequence of a coding sequence encoding an antimicrobial peptide may be easily predicted based on reference to the standard genetic code. When an antimicrobial peptide is to be expressed in a particular microbe, a nucleotide sequence encoding the antimicrobial peptide may be produced with reference to preferred codon usage for the particular microbe.

A coding sequence encoding an antimicrobial peptide may further include nucleotides encoding a secretion signaling protein, such that the antimicrobial peptide and the secretion signaling protein are fused and expressed as a single protein. A secretion signaling protein targets a protein for secretion out of the cell, and is usually present at the amino-terminal end of a protein. Secretion signaling proteins useful in prokaryotic microbes are known in the art and routinely used. Examples of secretion signaling proteins useful in lactic acid bacteria, including *L. lactis, Lb. acidophilus, Lb. acidophilus, Lb. bulgaricus, Lb. reuteri,* and *Lb. plantarum* are known. One example of a useful secretion signaling protein is from the protein Usp45 (Van Asseldonk et al., 1990, Gene, 95, 155-160). Several variations on Usp45 have been explored and may also be employed (Ng and Sarkar, 2012, Appl. Environ. Microbiol., 79:347-356). Additionally, *lactobacillus* secretion tags including but not limited to Lp_3050 and Lp_2145 may be used in *L. lactis* and Lactobacilli spp.

In addition to the signal peptides mentioned above which rely on the general Sec secretion machinery, many antimicrobial peptides also have their own dedicated secretion machinery with corresponding secretion tags. These tags are typically associated with the antimicrobial peptide natively secreted by these transport systems, however, these tags can also be used to secrete non-native antimicrobial peptides. An example of this mechanism of secretion is a double-glycine-type leader, which has been used to secrete colicin V from *L. lactis*. In the majority of microcin transport systems, secretion systems are associated with self-immunity or proteolytic cleavage of the microcin precursor. The Class II microcin gene clusters often encode for a dedicated ABC transporter and an accessory protein.

In embodiments herein, a coding sequence encoding an antimicrobial peptide may further include nucleotides encoding for genes for posttranslational modification and secretion of the peptide. For example, active microcin J25 (MJ25) production is dependent on the expression of four genes, mcjA, the microcin precursor, mcjB and mcjC which are required for necessary post-translational modifications of the precursor, and mcjD which confers immunity to MJ25 and facilitates secretion of the mature peptide.

In embodiments herein, genetically engineered bacteria can express and secrete one or more AMPs. In various embodiments herein, genetically engineered bacteria can express and secrete combinations of AMPs, such as two or more AMPs. In embodiments herein, a composition is included with a first genetically engineered bacteria expressing and secreting a first AMP and a second genetically engineered bacteria expressing and secreting a second AMP that is different than the first AMP. The first and second genetically engineered bacteria can include different heterologous promoters operably linked to polynucleotides encoding the AMPS providing for differential expression patterns of the AMPs through the intestinal tract (as described in greater detail below).

Using combinations of peptides may produce several benefits. Firstly, this approach can reduce the development of resistance of the pathogen to any one AMP. This is because resistance must simultaneously develop to multiple peptides for the pathogen to survive, an unlikely event. Additionally, some AMPs may act synergistically with each other thereby reducing the concentration of each peptide required. Lastly, it is possible that a given AMP may be inactive against the pathogen in different microenvironments. Because of the variations in physical and chemical properties in the different compartments of the gastrointestinal tract, the folding of antimicrobial peptides to a functionally active structure may be depended on the microenvironment.

A combination of AMPs with varying antimicrobial activity profiles can allow for more effective control of pathogens in the gastrointestinal tract of animals or humans.

Promoters and Sigma Factors

Naturally occurring bacteria monitor environmental conditions and they respond by modifying the expression pattern of their genes. Transcription of genes is carried out by a single species of RNA polymerase (RNAP). The core enzyme of RNAP executes RNA polymerization reactions, but it cannot recognize a DNA promoter, bind to it and initiate transcription. The task of promoter recognition in bacteria is left to one of a few protein subunits called sigma factors. Each sigma factor binds to its cognate promoter and connects with the RNAP core enzyme, forming the fully functioning RNAP holoenzyme. In *E. coli* there are seven known sigma factors and each bind to DNA promoters under different conditions. For example, Sigma 70 binds to its cognate DNA promoters at all times. Sigma 38 binds to its DNA cognate promoters in stationary state. Thus, expression of a gene of interest can be controlled by employing promoters that interact with sigma factors that are dominant under the desired expression condition. For example, by employing a promoter capable of binding sigma 38 but not sigma 70, gene expression would be upregulated in stationary phase rather than in exponential phase.

A complete list of known sigma factors in *E. coli* is presented in TABLE 5.

TABLE 5

Known Sigma Factors for *E. coli*

| Sigma factor | Gene | Purpose of Regulation |
|---|---|---|
| $\sigma^{19}$ | FecI | Regulates iron transport. |
| $\sigma^{24}$ | RpoE | Extracytoplasmic/extreme heat stress. |
| $\sigma^{28}$ | RpoF | Flagellar control |
| $\sigma^{32}$ | RpoH | Heat shock. |
| $\sigma^{38}$ | RpoS | Starvation/stationary phase. |
| $\sigma^{54}$ | RpoN | Nitrogen-limitation. |
| $\sigma^{70}/\sigma^4$ | RpoD | "Housekeeping" or primary sigma factor. |

Gruber T M, Gross C A (2003). "Multiple sigma subunits and the partitioning of bacterial transcription space". Annual Review of Microbiology. 57:441-66. doi: 10.1146/annurev.micro.57.030502.090913

The sigma factors of *E. coli* are exemplified above. However, it will be appreciated that each bacterium may have different sigma factors.

Promoters used herein include but are not limited to, high, medium, and low expression constitutive promoters, promoters that respond to stress, nutrient limitations, varying pH, varying osmotic pressure, and promoters that activate in stationary state.

A list of example promoters is presented in TABLE 6.

TABLE 6

| Examples of *E. coli* DNA promoters | | |
|---|---|---|
| Promoter | Description | Source |
| Constitutive | | |
| Anderson promoter library | Developed from library screen | 1 |
| P(Bla) | Ampicillin Resistance | 1 |
| P(Cat) | Chloramphenicol Resistance | 1 |
| P(Kat) | Kanamycin Resistance | 1 |
| PlacI | lacI promoter | 2 |
| PlacZ | lacZ promoter | 1 |
| PlacIQ | mutated lacI promoter | 3 |
| LacUV5 | high expression lacZ promoter | 4 |
| GlnRS | glutaminyl-tRNA synthetase | 1 |
| T7 | Phage | 1 |
| SP6 | Phage | 1 |
| PN25 | Phage | 5 |
| Exogenously-Induced | | |
| PBAD | Arabinose-Inducible | 1 |
| Plac | Lactose-Inducible | 1 |
| PTac | Lactose-Inducible | 1 |
| PTet, PTetO, PTetA | Tetracycline-Inducible | 1 |
| PTrp | Tryptophan-Inducible | 1 |
| PCpxP | Glucose-Inducible | 6 |
| Pm or Psal | Salicylate-Inducible | 7 |
| pH-Induced | | |
| PgadA | GadA promoter | 8 |
| PgadB | GadB promoter | 8 |
| PhdeA | HdeA promoter | 8 |
| Osmotic Pressure/Salt-Induced | | |
| PosmBp2 | OsmB promoter | 9 |
| Pgad | Chloride-Inducible promoter | 10 |
| PosmC | OsmC promoter | 11 |
| Anaerobically-Induced | | |
| PFnrS | small sRNA (FrnS) promoter | 12 |
| PynfEFG | YnfEGF operon promoter | 13 |
| pNirB | NirB promoter | 14 |
| ydfZ | YdfZ promoter | 13 |
| frdABCD | FrdABCD operon promoter | 13 |
| Starvation-Induced | | |
| osmBp2 | OsmB promoter | 9 |
| PmcjA | Microcin J25 mcjA native promoter | 15 |
| PmcjB | Microcin J25 mcjB native promoter | 15 |
| PmcjC | Microcin J25 mcjC native promoter | 15 |
| PyciG | YciG promoter | 16 |
| PkatE | KatE promoter | 16 |
| PgadA | GadA promoter | 16 |
| PosmY | OsmY promoter | 16 |
| Temperature-Induced | | |
| pTlpA | Induced at high temperatures | 17 |
| pR-pL | Induced at high temperatures | 18 |
| Inflammation-Induced | | |
| pYeaR | Nitrite/Nitrate-Inducible | 19 |
| pTTrBCA | Tetrathionate + Anaerobic (Inflammation) | 20 |
| Quorum-Sensing | | |
| pluxI and PlasI | Responds to AHL from Pseudomonas | 21 |
| PtpQrr4 | Responds to CAI-1 from Vibrio cholerae | 22 |

Sources for TABLE 6:

1. http://parts.igem.org/Promoters/Catalog/Ecoli/Constitutive
2. Tunable thermal bioswitches for in vivo control of microbial therapeutics
3. A synthetic bacterial information transfer system functions in the mammalian gut 4. Isolating *Escherichia coli* strains for recombinant protein production
5. Functional dissection of *Escherichia coli* promoters: information in the transcribed region is involved in late steps of the overall process
6. Detection of pathological biomarkers in human clinical samples via amplifying genetic switches and logic gates
7. In vivo gene regulation in *Salmonella* spp. by a salicylate-dependent control circuit
8. Gene Expression Profiling of the pH Response in *Escherichia coli*
9. Multistress Regulation in *Escherichia coli*: Expression of osmB Involves Two Independent Promoters Responding either to σS or to the RcsCDB His-Asp Phosphorelay
10. A chloride-inducible gene expression cassette and its use in induced lysis of *Lactococcus lactis*.
11. Osmotic induction of gene osmC expression in *Escherichia* coliK12
12. Translational Regulation of Gene Expression by an Anaerobically Induced Small Non-coding RNA in *Escherichia coli*
13. Genome-Wide Expression Analysis Indicates that FNR of *Escherichia coli* K-12 Regulates a Large Number of Genes of Unknown Function
14. Construction of a Synthetically Engineered nirB Promoter for Expression of Recombinant Protein in *Escherichia coli*
15. Growth-Phase-Dependent Expression of the Cyclopeptide Antibiotic Microcin J25
16. Classification and Strength Measurement of Stationary-Phase Promoters by Use of a Newly Developed Promoter Cloning Vector
17. A proteinaceous gene regulatory thermometer in *Salmonella*.
18. Production of recombinant proteins in *E. coli* by the heat inducible expression system based on the phage lambda pL and/or pR promoters
19. Characterization of a rationally engineered nitric oxide, nitrate and nitrite biosensor linked to a hybrid bacterial mammalian promoter
20. Programmable bacteria detect and record an environmental signal in the mammalian gut
21. A sensing array of radically coupled genetic 'biopixels', Reprogramming microbes to be pathogen-seeking killers
22. Repurposing a Two-Component System-Based Biosensor for the Killing of *Vibrio cholerae*.

For example, constitutive promoters J23100-109 (SEQ ID NOS: 3-5) perform best in nutrient-rich environments of the GI tract-their differences in strength of gene expression are also used as a way to produce antimicrobial peptides, maturation factors and secretion machinery at the most optimal ratios.

The FNR promoter (SEQ ID NO: 6) acts as a constitutive control in the most anerobic environments of the GI tract, as it originates from a switch system in *E. coli* between aerobic and anaerobic metabolism, the FNR regulon.

For example, GadA/B promoters (SEQ ID NOS: 7-8) are pH sensitive, which makes them useful for the highly acidic components of the GI tract.

In various embodiments herein, rpoS promoters can be used. In various embodiments herein, anaerobically-inducible promoters can be used. In various embodiments herein, chloride-inducible promoters can be used. In various embodiments herein, stationary-phase promoters can be used.

Promoter osmB (SEQ ID NO: 9) is a stress-responsive rpoS promoter intended for nutrient-poor environments with a high salt/ion content (osmotic stress).

In various embodiments herein, genetically engineered bacteria can express and secrete one or more AMPs. The first and second genetically engineered bacteria can include different heterologous promoters operably linked to polynucleotides encoding the AMPs providing for differential expression patterns of the AMPS through the intestinal tract.

Administering all of these systems in combination results in the highest overall production and secretion of antimicrobial peptides in the GI tract. A combination of genetically engineered bacteria that express and secrete AMPs out of promoters that respond to different gut microenvironments can allow for more effective control of pathogens in the gastrointestinal tract of animals or humans.

Aspects may be better understood with reference to the following examples. These examples are intended to be representative of specific embodiments, but are not intended as limiting the overall scope of embodiments herein.

EXAMPLES

Example 1. Engineered Bacteria Expressing and Secreting Antimicrobial Peptides Using Different Promoters Exhibiting Different Activities in Different Environments Herein, we describe the application of this invention for the delivery of the antimicrobial peptide microcin J25 (MJ25) to the intestines of animals or humans.

MJ25 is a bacteriostatic peptide with activity against *Salmonella* spp. Application of this invention results in low counts of *Salmonella* spp. in the digestive tract of animals or humans.

Under its native expression system (as shown in FIG. 1), MJ25 is naturally produced by Gram-negative bacteria *Escherichia coli* under nutrient deficient conditions to inhibit growth of other phylogenetically-similar Gram-negative bacteria, including *Salmonella* spp. The system's native expression system results in high levels of MJ25 production in the stationary phase when nutrients in the environment have been depleted.

Surprisingly, it has been determined herein that the native promoter does not result in strong activity against *Salmonella* spp. in microenvironments of the GI tract. Equally surprising, it has been determined herein that constitutive promoters do not often result in activity against *Salmonella* spp. in microenvironments of the GI tract.

In embodiments herein, new MJ25 expression vectors are included for various *E. coli* probiotic species with the expression of all parts relying on recombinant expression systems.

As an example, embodiments herein include genetically engineered *E. coli* Symbioflor G3, genetically engineered Symbioflor G5, genetically engineered Symbioflor G*, or genetically engineered *E. coli* Nissle 1917.

These bacteria have been engineered to express and secrete microcin MJ25. In embodiments herein, the DNA promoter used in a recombinant construct for the expression of MJ25 is chosen from promoters presented in TABLE 6, including but not limited to the following group: constitutive (SEQ ID NOS: 3-5), FNRs (SEQ ID NO: 6), stationary phase (SEQ ID NO: 11), GadA/B (SEQ ID NOS: 7-8), and OsmB (SEQ ID NO: 9).

Figure 2:
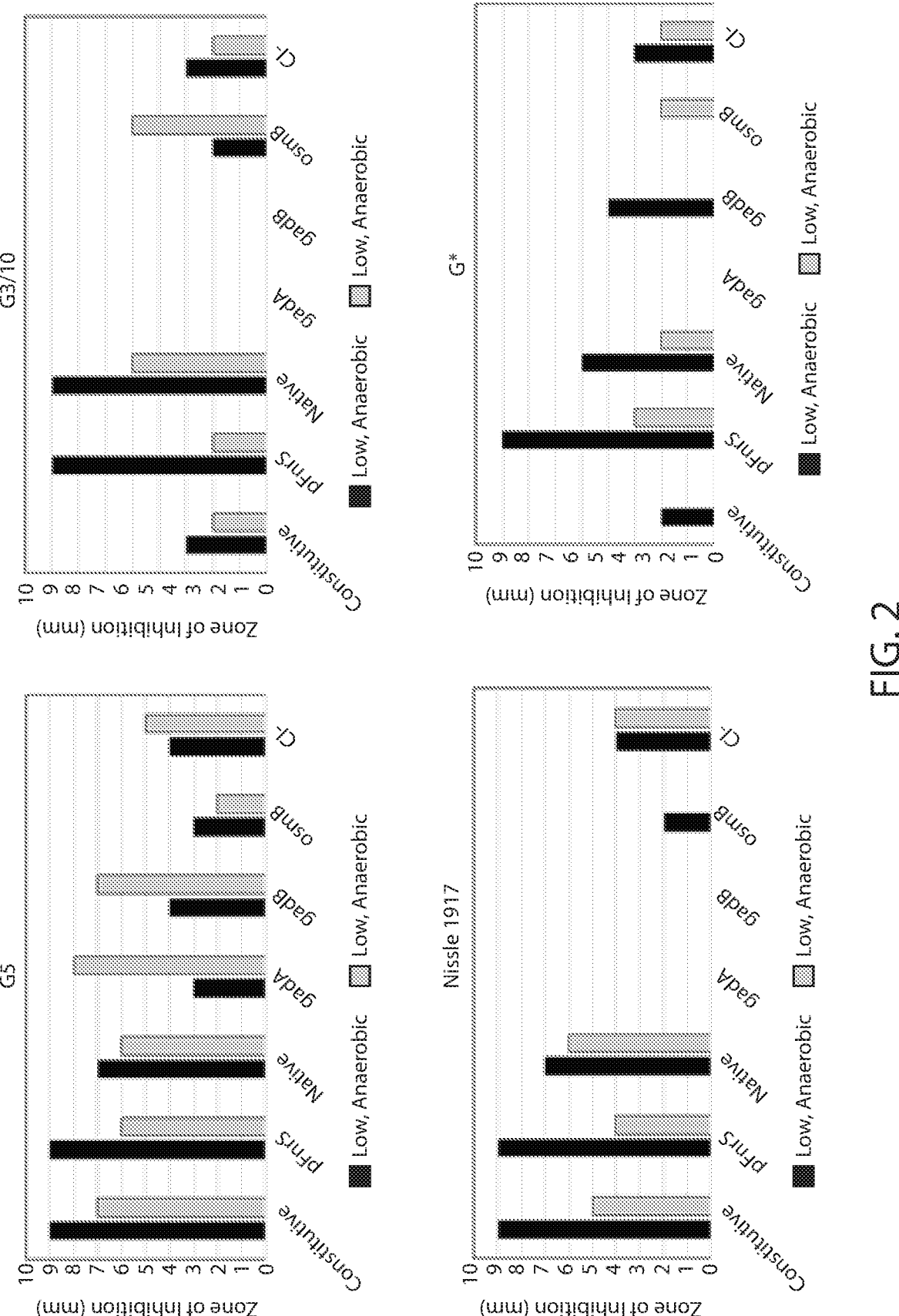
FIG. 2 depicts agar diffusion assay results of *E. coli* Symbioflor G3/10 and G5 with different promoters in two different environments

The antimicrobial activity of genetically engineered bacteria against *Salmonella enterica enterica Enteritidis* was measured as discussed in Example 11. In FIG. 2, the activities are shown of genetically engineered bacteria either in aerobic conditions with rich media, or in anaerobic conditions with poor media. In specific, FIG. 2 shows expected agar diffusion assay results of four genetically engineered probiotic strains of *E. coli* (G5, G3/10, G*, and Nissle 1917) against *Salmonella enterica Enteritidis*. Each of the four *E. coli* strains is engineered with different promoters controlling the expression of MJ25 (constitutive, FNR, native, gadA, gadB, osmB, and chloride-inducible). Assays are performed in two different environments (rich nutrient, aerobic environment and low nutrient, anaerobic environment).

It is observed that the activity varies for each system as the environmental conditions change. The activity, which is directly related to the amount of MJ25 expressed by the engineered bacteria, often varies in surprising ways.

For example, the constitutive promoter is expected to express high levels of MJ25 in rich media in aerobic conditions. Indeed, Nissle 1917 and G5 express MJ25 strongly from a constitutive promoter under the conditions. However, unexpectedly, G3 and G* express MJ25 poorly out of the same constitutive promoter in rich media and aerobic conditions.

In another example, the native promoter for MJ25 expression is known to express MJ25 when nutrients are depleted. However, it was observed that G3 and G* express MJ25 out of the native promoter more strongly in rich media than in poor media.

We observe that there is significant, unpredictable variance in activity, depending on the conditions, the promoter and the probiotic strain used.

TABLE 7 compares the MJ25 production by 12 different probiotics (four strains with three promoters) under low-nutrient conditions using a supernatant inhibition assay (detailed in Example 11). These data suggest that on average, the low nutrient promoter outperforms the other promoters in a low-nutrient environment. This is as expected.

What is unexpected is that probiotic 1 expresses MJ25 more strongly out of a high-nutrient promoter than out of the low-nutrient promoter. What is also unexpected is that probiotic 2 expresses MJ25 equally strongly out of a constitutive promoter as it does out of the low-nutrient promoter.

TABLE 7

Activities of Probiotics Against SE under Low-Nutrient Conditions

| Promoter: | Prob. 1 | Prob. 2 | Prob. 3 | Prob. 4 | Avg. Performance |
|---|---|---|---|---|---|
| Low-Nutrient | 320 | 1280 | 1280 | 1280 | 1040 |
| Constitutive | 320 | 1280 | 320 | 80 | 500 |
| High-Nutrient | 1280 | 640 | 10 | 160 | 522.5 |

Figure 3:
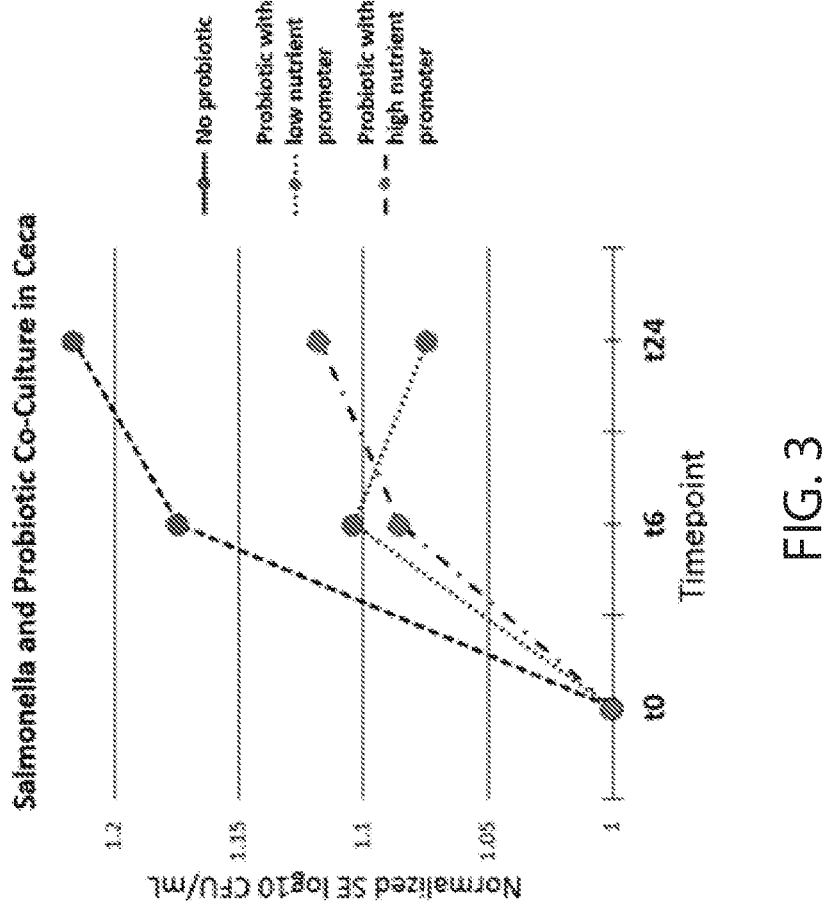
FIG. 3 shows *Salmonella enterica* serovar *Enteritidis* growth in a biomatrix assay in the absence of probiotic, in the presence of probiotic expressing antimicrobial peptide MJ25 under a low nutrient promoter, and in the presence of probiotic expressing MJ25 under a high nutrient promoter. Details of the experimental protocol are presented in Example 13.

FIG. 3 shows the effect of individual probiotics against *Salmonella enterica* serovar *Enteritidis* (SE) in a biomatrix assay mimicking the GI tract environment (biomatrix assay described in Example 13). Is specific, FIG. 3 shows *Salmonella Enteritidis* growth in a biomatrix assay in the absence of probiotic, in the presence of probiotic expressing MJ25 under a low nutrient promoter, and in the presence of probiotic expressing MJ25 under a high nutrient promoter. Details of the experimental protocol are presented in Example 13. The probiotic with the high nutrient promoter shows improved activity earlier while the low nutrient promoter probiotic shows greater activity later in the incubation. The constitutive and starvation promoters have maximum activity at different times. This is due to a change in nutrient availability in the cecal content.

We inferred that a combination of these two systems may result in an overall improved activity over time compared to the activity of each individual system.

Figure 4:
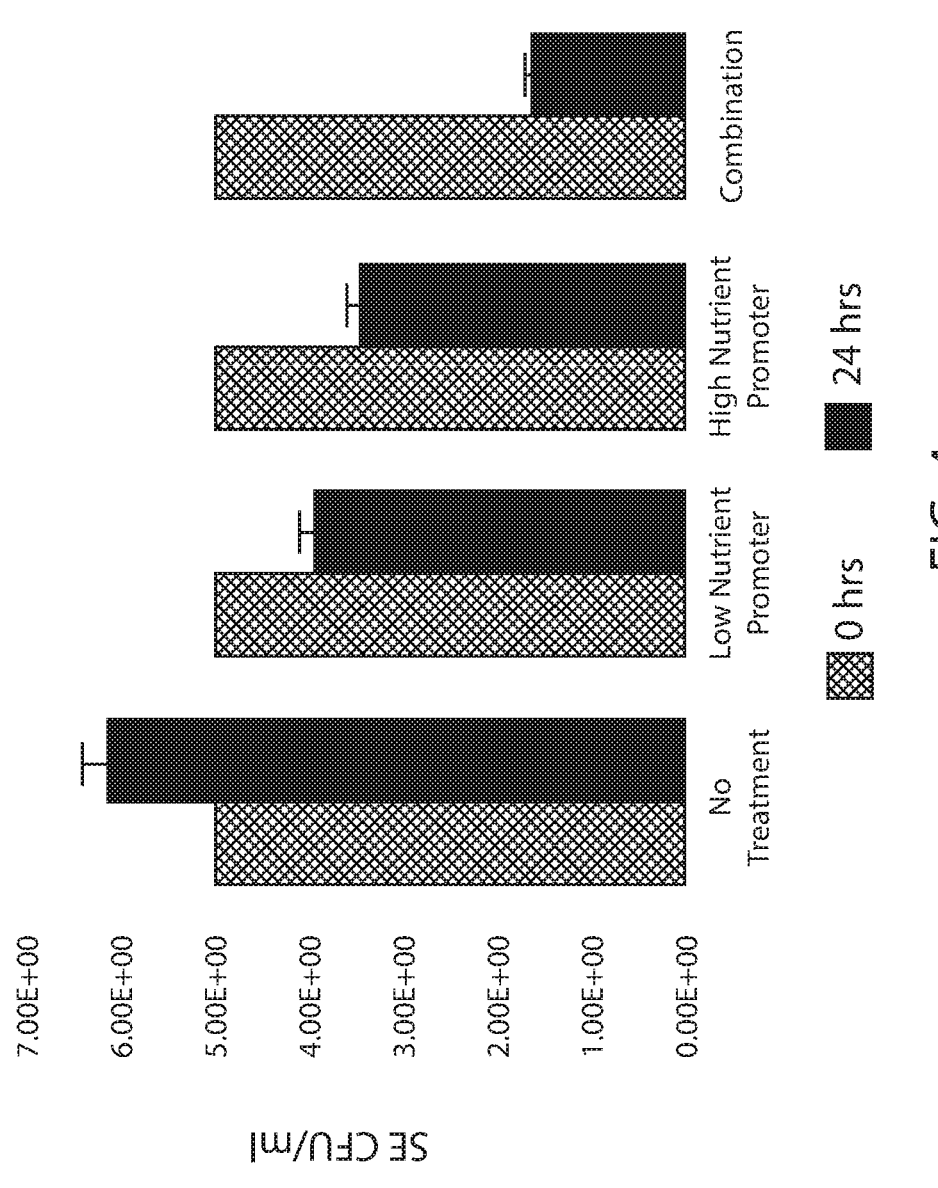
FIG. 4 shows relative *Salmonella enterica* serovar *Enteritidis* growth in a biomatrix assay in the absence of probiotic, in the presence of probiotic expressing MJ25 under a low nutrient promoter, in the presence of probiotic expressing MJ25 under a high nutrient promoter and in the presence of a combination of the two probiotics. All counts at 0 hours are normalized to 5.00E+6 CFU/ml.

FIG. 4 shows the relative counts of SE at two different points (0 and 24 hours) in four distinct biomatrix assay experiments. In the first experiment, there is no additional treatment. SE grows inside the cecal content over 24 hours, with its counts (CFU/ml of sample) increasing from 5.00E+6 to approximately 6.00E+6. In the second experiment SE is inhibited by MJ25 produced from a low nutrient promoter. In the third experiment, SE is inhibited by MJ25 produced from a high nutrient promoter. In the fourth experiment, SE is inhibited by MJ25 produced by a combination of the low nutrient promoter and the high nutrient promoter.

This example also shows that a combination of high and low nutrient promoters has the best overall negative effect on SE counts. By combining the two systems, the maximum effect is attained for a longer period of time, ultimately resulting in a greater reduction of *Salmonella*. This example may be analogous to nutrient fluctuations observed in the GI tract over time.

TABLE 8 shows the distribution of genetically engineered strains in ceca of treated chickens. TABLE 9 shows the prevalence of these genetically engineered probiotics in chicken. The experimental protocol is detailed in Example 15.

Strain distributions differed across birds fed a composition consisting of a mixture of genetically engineered probiotics. This suggests that different strains of the same species survive or colonize better in different birds despite identical rearing conditions. Probiotic prevalence (% of birds with detectable probiotic levels) in birds fed a mixture was nearly double that compared to birds fed with the single strain. This cannot be solely attributed to Nissle 1917, G3/10, and G* simply outperforming G5 colonization because G5 was regularly detected in birds fed the mixture. It is likely that administering combinations of different strains enables greater overall colonization by accommodating for the bird to bird variability observed in the strain distribution data.

Alternatively stated, a composition comprising of a combination of engineered probiotics better ensures that each bird receives a strong colonizer for that individual animal.

TABLE 8

Strain distributions recovered from ceca

| Strain | Mixture | | G5 only | |
| | Bird 1 | Bird 2 | Bird 1 | Bird 2 |
|---|---|---|---|---|
| Nissle 1917 | 0.9 | 0.5 | | |
| G5 | | 0.5 | 1.0 | 1.0 |
| G3/10 | 0.1 | | | |
| G* | | | | |

TABLE 9

| Probiotic Prevalence | | | |
| --- | --- | --- | --- |
| Treatment | >10 colonies | Any colonies | % of birds |
| Mixture | 8 of 12 | 11 of 12 | 91.67 |
| G5 only | 4 of 12 | 7 of 12 | 58.33 |

Figure 5:
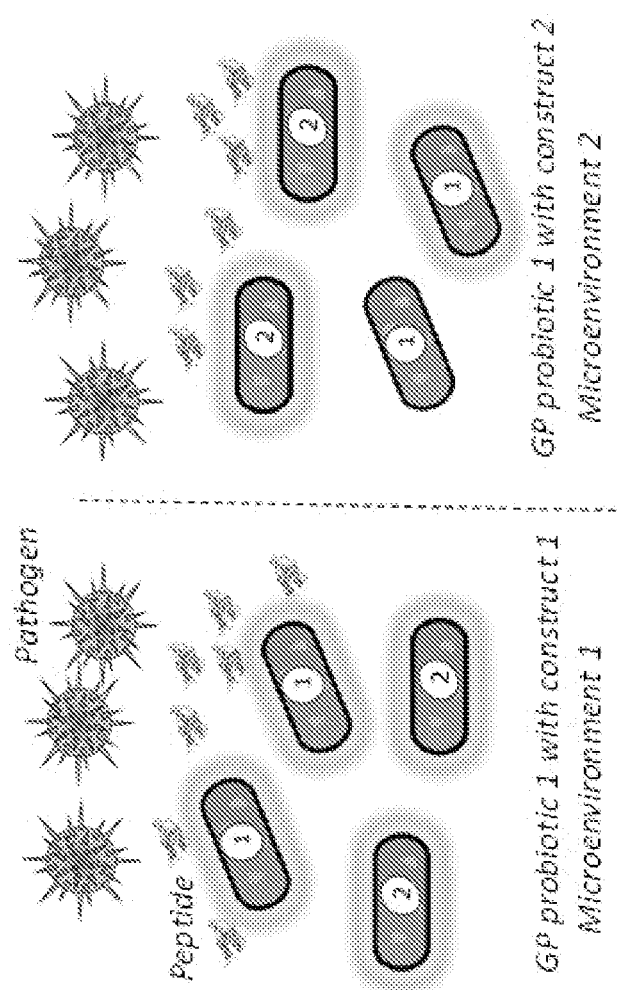
FIG. 5 is a depiction of a mixture of genetically engineered probiotics expressing peptides from different constructs in response to different microenvironments. In this example, the probiotic organisms are identical. The antimicrobial peptide is identical in both systems. The promoters used are different. In construct 1, the promoter is responsive to Microenvironment 1, whereas in construct 2, the promoter is responsive to Microenvironment 2. As a result, in Microenvironment 1, the probiotic carrying construct 1 produces more peptide than probiotic carrying construct 2. In contrast, in Microenvironment 2 the probiotic carrying construct 2 produces more peptide than probiotic carrying construct 1. The effective result is the elimination of the pathogenic microbe in both microenvironments.

Example 2. Combinations of Engineered Bacteria Expressing and Secreting Antimicrobial Peptides Using Different Promoters have Improved Activities in Different Environments In various embodiments herein, depicted in FIG. 5, a combination of genetic constructs is designed for high production of antimicrobial peptides in response to different environments to achieve elimination of pathogenic bacteria in the GI tract of animals or humans. In specific, FIG. 5 shows a depiction of a mixture of genetically engineered probiotics expressing peptides from different constructs in response to different microenvironments. In this example, the probiotic organisms are identical, the antimicrobial peptide is identical, but the promoters used are different. In construct 1, the promoter is responsive to Microenvironment 1, whereas in construct 2, the promoter is responsive to Microenvironment 2. As a result, in Microenvironment 1, the probiotic carrying construct 1 produces more peptide than probiotic carrying construct 2. In contrast, in Microenvironment 2 the probiotic carrying construct 2 produces more peptide than probiotic carrying construct 1. The effective result is the elimination of the pathogenic microbe in both microenvironments.

In various embodiments herein, a composition is included with a first genetically engineered E. coli expressing and secreting MJ25 and a second genetically engineered E. coli expressing and secreting MJ25. The first and second genetically engineered bacteria include different heterologous promoters operably linked to polynucleotides encoding MJ25 providing for differential expression patterns of MJ25 through the intestinal tract.

The GI tract has compartments with high nutrients, such as the duodenum. The GI tract has compartments with low nutrients, such as the cecum. Low nutrient responsive promoters may not result in adequate expression in the duodenum or parts of the GI tract with high nutrient availability. Conversely, constitutive and high nutrient responsive promoters may not result in adequate expression in the cecum, or in other certain parts of the GI tract with low nutrient availability.

When treated with these combinations of probiotics with different expression patterns, MJ25 can reach a much broader area of the GI tract thus increasing chances of killing Salmonella cells hiding in hard to reach niches.

We have proved that these combinations are more active against Salmonella spp. than individual genetically engineered probiotics. This was demonstrated by testing the activity of the engineered E. coli carrying the constitutive promoter in low nutrient bio-matrix assays where inadequate Salmonella spp. reduction in vitro was seen. Low levels of reduction of Salmonella spp. in high nutrient bio-matrix assays by the engineered E. coli carrying the low nutrient responsive promoter (Example 1) were also observed.

The best results were observed when both types of promoters in the same bio-matrix assay were used. At first, the high nutrient responsive promoters jump-start microcin production and once most available nutrients are depleted the low-nutrient responsive promoters continue to produce microcin thereby suppressing SE growth. This combination method works better than using either system on its own.

In one embodiment, the first genetically engineered E. coli expresses MJ25 under the control of constitutive promoter J23100 (SEQ ID NO: 3), and the second engineered E. coli expresses MJ25 under the control of stationary promoter FNR (SEQ ID NO: 6).

In one embodiment, the first genetically engineered E. coli expresses MJ25 under the control of constitutive promoter J23100 (SEQ ID NO: 3), and the second genetically engineered E. coli expresses MJ25 under the control of a stationary-phase responsive promoter originating from the native MJ25 secretion system (SEQ ID NO: 10).

Certain parts of the GI tract are more acidic than others. However, pathogens can still lurk around in highly acidic regions. In various embodiments herein, the promoters are acid stress pH-response promoters, and starvation-responsive promoters. In various embodiments described herein, the promoters are chloride responsive promoters, since certain parts of the colon may have high concentrations of chloride.

In one embodiment, the first genetically engineered E. coli expresses MJ25 under the control of constitutive promoter J23100 (SEQ ID NO: 3), and the second genetically engineered E. coli expresses MJ25 under the control of GadA promoter (SEQ ID NO: 7).

In one embodiment, the first genetically engineered E. coli expresses MJ25 under the control of constitutive promoter J23100 (SEQ ID NO: 3), and the second genetically engineered E. coli expresses MJ25 under the control of GadB promoter (SEQ ID NO: 8).

In one embodiment, the first genetically engineered E. coli expresses MJ25 under the control of constitutive promoter J23100 (SEQ ID NO: 3), and the second genetically engineered E. coli expresses MJ25 under the control of OsmB promoter (SEQ ID NO: 9).

In one embodiment, the first genetically engineered E. coli expresses MJ25 under the control of low-nutrient promoter FNR (SEQ ID NO: 6), and the second genetically engineered E. coli expresses MJ25 under the control of promoter GadA (SEQ ID NO: 7).

Example 3. Combinations of Engineered Bacteria Expressing and Secreting Antimicrobial Peptides In various embodiments herein, depicted in FIG. 6, a composition is included with a first genetically engineered bacterium expressing and secreting an antimicrobial peptide and a second genetically engineered bacterium expressing and secreting the same antimicrobial peptide. The first and second genetically engineered bacteria may belong to different species.

Figure 6:
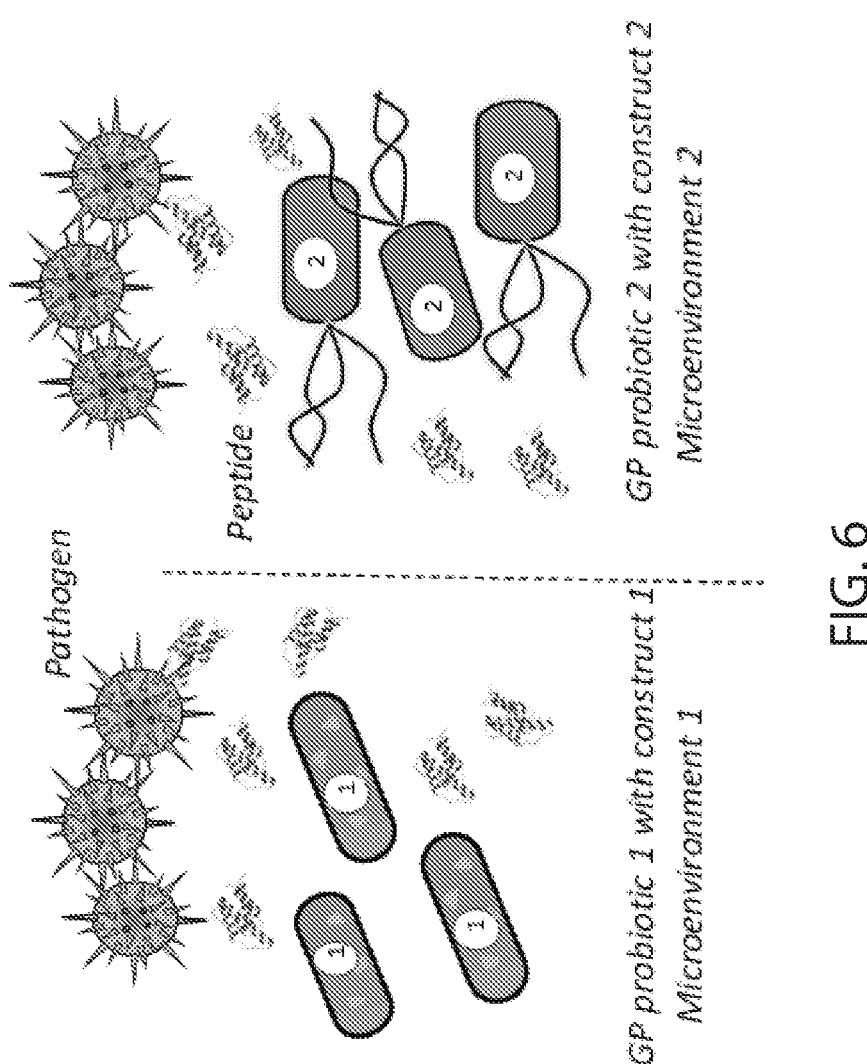
FIG. 6 is a depiction of a combination of different probiotics expressing peptides in response to different microenvironments. In this example, the probiotic organisms are selected to be better adapted to two distinct microenvironments. As a result, probiotic 1 colonizes Microenvironment 1, whereas probiotic 2 colonizes Microenvironment 2, such that probiotic 1 is in higher counts in Microenvironment 1, whereas probiotic 2 is in higher counts in Microenvironment 2. The overall effect is that the antimicrobial peptide is expressed in high counts by genetically engineered bacteria in both microenvironments. The result is thus the elimination of the pathogenic microbe in both microenvironments.

In specific, FIG. 6 shows a depiction of a combination of different probiotics expressing peptides in response to different microenvironments. In this example, the probiotic organisms are selected to be better adapted to two distinct microenvironments. As a result, probiotic 1 colonizes Microenvironment 1, whereas probiotic 2 colonizes Microenvironment 2, such that probiotic 1 is in higher counts in Microenvironment 1, whereas probiotic 2 is in higher counts in Microenvironment 2. The overall effect is that the antimicrobial peptide is expressed in high counts by genetically engineered bacteria in both microenvironments. The result is thus the elimination of the pathogenic microbe in both microenvironments. The first and second genetically engineered bacteria are chosen to have different profiles of colonization in the GI tract of animals or humans. The first bacterium is chosen to reside and colonize in one distinct microenvironment in the GI tract of animals or humans. The second bacterium is chosen to reside and colonize a second distinct microenvironment in the GI tract of animals or humans. In one embodiment, the first genetically engineered bacterium is *Escherichia coli* Nissle 1917, and the second engineered bacterium is *Escherichia coli* Symbioflor G3.

In one embodiment, the first genetically engineered bacterium is *Escherichia coli* Nissle 1917, and the second engineered bacterium is *Bacillus subtilis.*

In one embodiment, the first genetically engineered bacterium is *Escherichia coli* Nissle 1917, and the second engineered bacterium is *Lactobacillus acidophilus.*

In one embodiment, the first genetically engineered bacterium is *Escherichia coli* Nissle 1917, and the second engineered bacterium is *Enterococcus faecalis.*

Example 4. Combinations of Engineered Bacteria Expressing and Secreting Antimicrobial Peptides In various embodiments herein, depicted in FIG. 7, a composition is included with a first genetically engineered bacterium expressing and secreting an antimicrobial peptide and a second genetically engineered bacterium expressing and secreting the same antimicrobial peptide. The first and second genetically engineered bacteria may belong to the different species.

Figure 7:
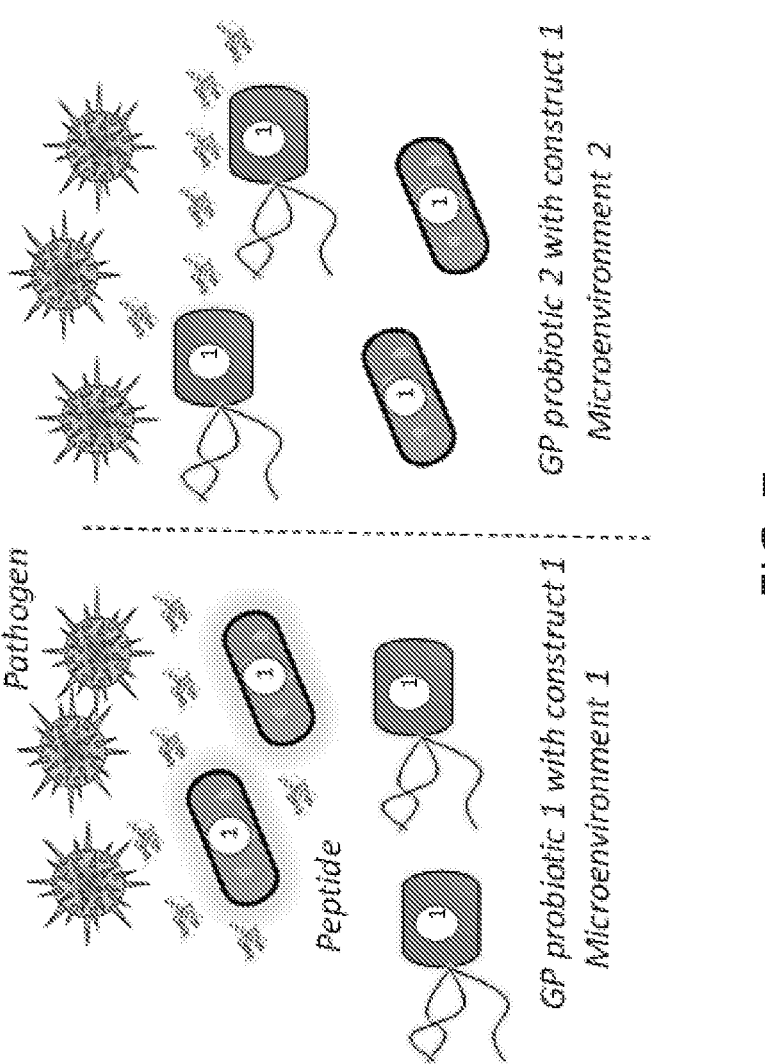
FIG. 7 is a depiction of a mixture of probiotics expressing peptides from the same DNA construct. The probiotics express the antimicrobial peptide in response to different microenvironments. In Microenvironment 1, probiotic 1 produces more peptide than probiotic 2 while in Microenvironment 2 probiotic 2 produces more peptide. The result is thus the elimination of the pathogenic microbe in both microenvironments.

In specific, FIG. 7 shows a depiction of a mixture of probiotics expressing peptides from the same construct. The probiotics express the antimicrobial peptide in response to different microenvironments. In Microenvironment 1, probiotic 1 produces more peptide than probiotic 2 while in Microenvironment 2 probiotic 2 produces more peptide. The result is thus the elimination of the pathogenic microbe in both microenvironments.

The bacteria are chosen to have different capacities to express and secrete antimicrobial peptides in different microenvironments. The first bacterium is chosen to express and secrete antimicrobial peptides in one distinct microenvironment in the GI tract of animals or humans. The second bacterium is chosen to express and secrete antimicrobial peptides in a second distinct microenvironment in the GI tract of animals or humans.

In one embodiment, the first genetically engineered bacterium is *Escherichia coli* Nissle 1917, and the second engineered bacterium is *Bacillus subtilis* 168.

In one embodiment, the first genetically engineered bacterium is a poultry isolate *E. coli*, and the second engineered bacterium is *Lactobacillus pullorum.*

In one embodiment, the first genetically engineered bacterium is a *Bifidobacterium* spp., and the second engineered bacterium is *Lactococcus lactis.*

Example 5. Combinations of Engineered Bacteria Expressing and Secreting Different Antimicrobial Peptides Have Improved Activities in Different Environments In various embodiments herein, depicted in FIG. 8, a composition is included with a first genetically engineered bacterium expressing and secreting an antimicrobial peptide and a second genetically engineered bacterium expressing and secreting a different antimicrobial peptide.

Figure 8:
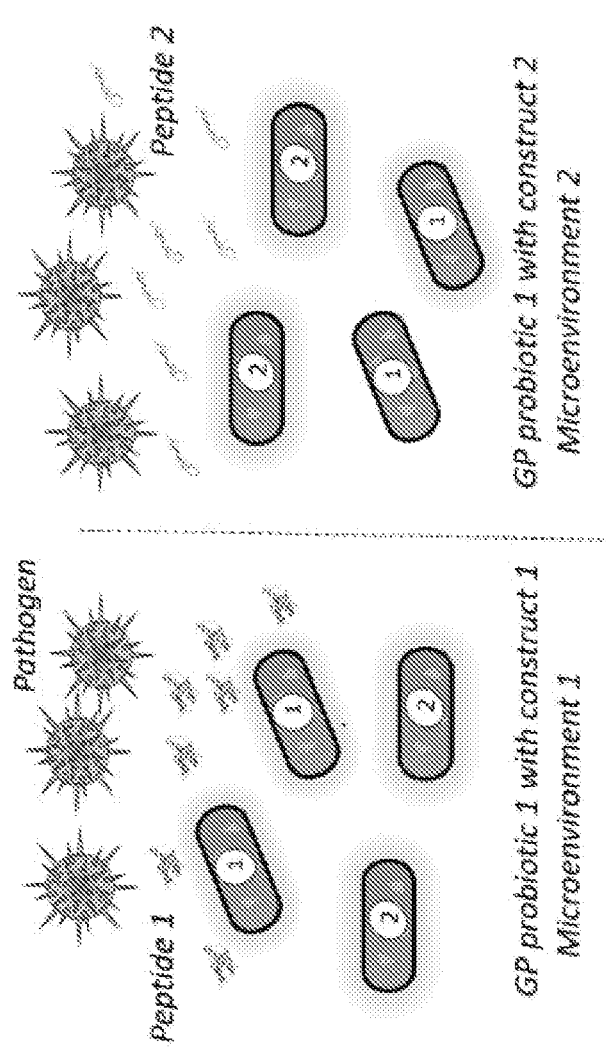
FIG. 8 shows a depiction of a combination of genetically engineered probiotics expressing different peptides from the same construct. Probiotic 1 expresses antimicrobial peptide 1 (AMP1). Probiotic 2 expresses antimicrobial peptide 2 (AMP2). AMP1 is chosen to be active in Microenvironment 1, whereas AMP2 is chosen to be active in Microenvironment 2. The result is thus the elimination of the pathogenic microbe in both microenvironments.

In specific, FIG. 8 shows a depiction of a combination of genetically engineered probiotics expressing different peptides from the same construct. Probiotic 1 expresses antimicrobial peptide 1 (AMP1). Probiotic 2 expresses antimicrobial peptide 2 (AMP2). AMP1 is chosen to be active in microenvironment 1, whereas AMP2 is chosen to be active in microenvironment 2. The result is thus the elimination of the pathogenic microbe in both microenvironments.

This combination of genetic constructs is designed for high production of two different peptides that are active in response to different environments to achieve elimination of *Salmonella* Spp. in the GI tract of poultry.

In various embodiments herein, a composition is included with a first genetically engineered probiotic expressing and secreting a first antimicrobial peptide and a second genetically engineered probiotic expressing and secreting a second. The first and second antimicrobial peptides are active against *Salmonella* spp. inside different microenvironments of the GI tract.

In one embodiment, the first genetically engineered probiotic expresses and secretes MJ25, and the second engineered probiotics expresses and secretes protegrin. These two peptides are expected to be degraded inside different microenvironments of the GI tract.

In one embodiment the first genetically engineered probiotic produces MJ25 and the second genetically engineered probiotics produces Microcin N.

In one embodiment the first genetically engineered probiotic produces MJ25 and the second genetically engineered probiotics produces Microcin L.

In one embodiment the first genetically engineered probiotic produces MJ25 and the second genetically engineered probiotics produces Protegrin 1.

Figure 9:
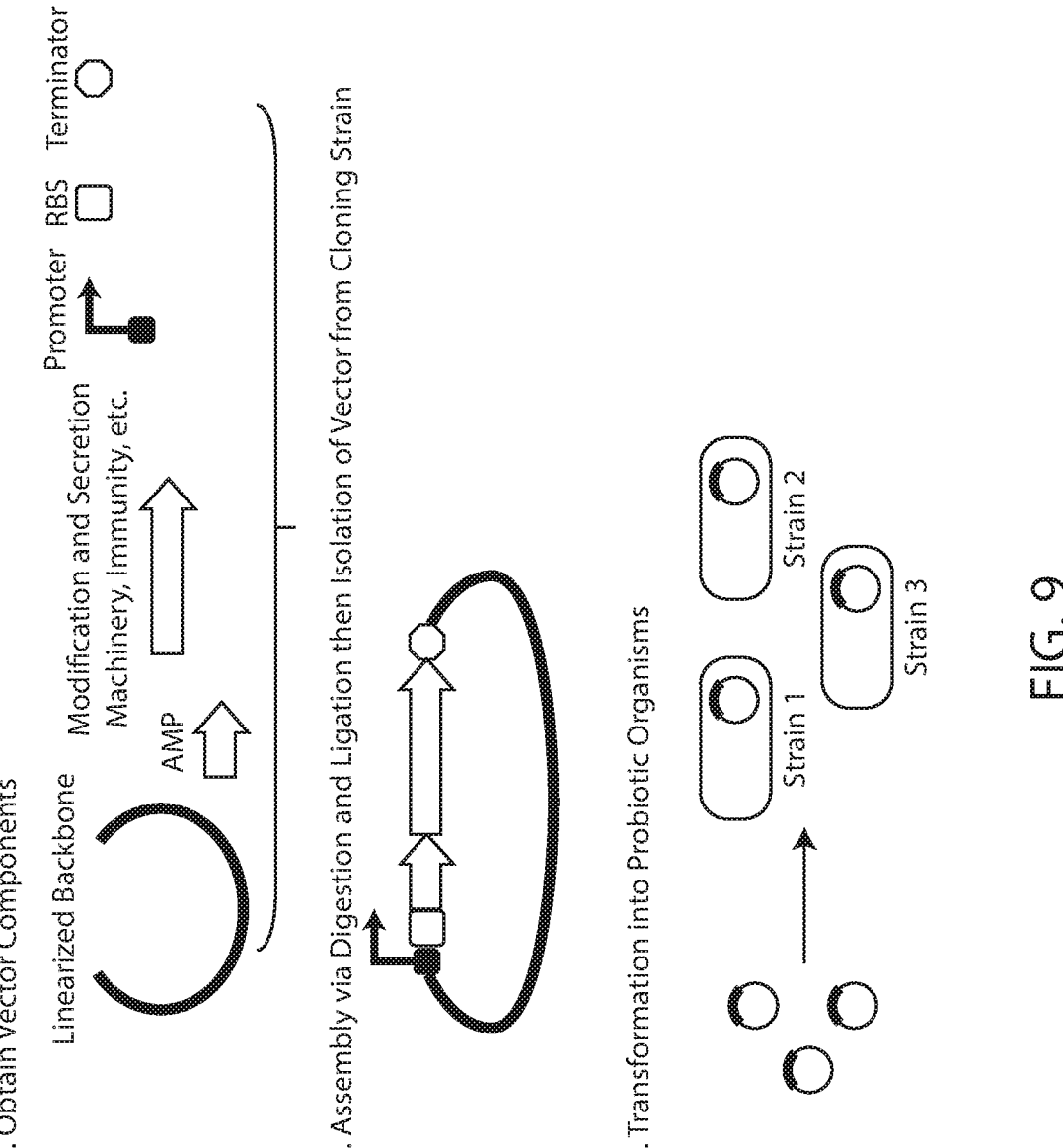
FIG. 9 shows the construction of AMP production vectors and generation of probiotic library. Core genetic components are first assembled using standard cloning techniques. The assembly reaction is typically transformed into a cloning intermediate to propagate the final vector. This vector is then isolated and transformed into a library of compatible probiotic organisms.

Example 6. Construction of AMP Expression Vectors and Insertion into Probiotics FIG. 9 is a schematic depicting an overview of the process for constructing AMP expression vectors and engineered probiotics. In specific, FIG. 9 shows the construction of AMP production vectors and generation of probiotic library. Core genetic components are first assembled using standard cloning techniques. The assembly reaction is typically transformed into a cloning intermediate to propagate the final vector. This vector is then isolated and transformed into a library of compatible probiotic organisms.

The process is as follows. A linearized plasmid backbone is obtained, for example by polymerase chain reaction (PCR) or restriction digest. The DNA encoding promoters, ribosomal binding sites, genes, and terminators are then obtained by either direct DNA synthesis or by PCR from an existing template. Genes include the AMP gene and in many cases secretion machinery and immunity genes. These components are then digested with restriction enzymes compatible with the linearized backbone and the components are ligated. The order of assembly into the final construct is not of importance to the final invention.

The ligation product is then transformed into an *E. coli* cloning strain (e.g. *E. coli* Top Ten, *E. coli* DH5A, *E. coli* MC1061 F', *E. coli* JM109, *E. coli* DH10B) for example by heat shock or electroporation. A clone containing the correct final AMP-expression vector is verified by colony PCR and Sanger DNA sequencing. The clone is grown to propagate the AMP-expression vector and the vector is then isolated using a standard Miniprep procedure. The vector is then transformed into the probiotic organism of choice for example by electroporation. This process can be repeated to incorporate a variety of expression parts (ex. different promoters, ribosomal binding sites, genes, terminators). Note that in FIG. 8 all genes are expressed as a single operon. Genes can also be expressed as separate transcriptional units on the same vector.

Example 7. Construction of Microcin J25 Production Vectors (pGPMJ25) with Various Promoters To generate pGPMJ25, mcjA (SEQ ID NO: 1) and mcjBCD (SEQ ID NO: 2) was inserted into plasmid backbone with promoters responding to different microenvironments. In one construct, mcjA and mcjBCD genes were expressed under constitutive promoters which are active in the presence of ample nutrients. In another construct, mcjA and mcjBCD genes were expressed under promoters known to be activated under starvation conditions. Between different genetic constructs, the backbone and mcjA and mcjBCD components remained the same. The final constructs are then transformed into probiotic *E. coli* (ex. *E. coli* Nissle 1917).

Example 8: Preparation of Composition for Treatment of an Animal Including First Genetically Engineered Bacterium and Second Genetically Engineered Bacterium Two probiotic organisms harbor two distinct genetic constructs. For example, one *E. coli* carries the pH sensitive system, and another *E. Coli* caries the anerobic responsive system. The two engineered probiotics are grown overnight, and then combined in a single concoction that is administered orally to animals either preventatively or therapeutically.

Example 9. Combining Multiple Expression Systems in a Single Organism as an Alternative to Using Mixtures of Engineered Organisms In various embodiments herein, a single probiotic is transformed with both, or a single genetic construct containing two copies of the MJ25 genes, each copy with a different responsive promoter or RBS sequence. This better ensures the probiotic is capable of expressing the AMPs under multiple conditions encountered in the intestines while avoiding the requirement of multiple probiotic strains

Example 10: Methods for Assessing AMP Production: Agar Diffusion Assay

Figure 10:
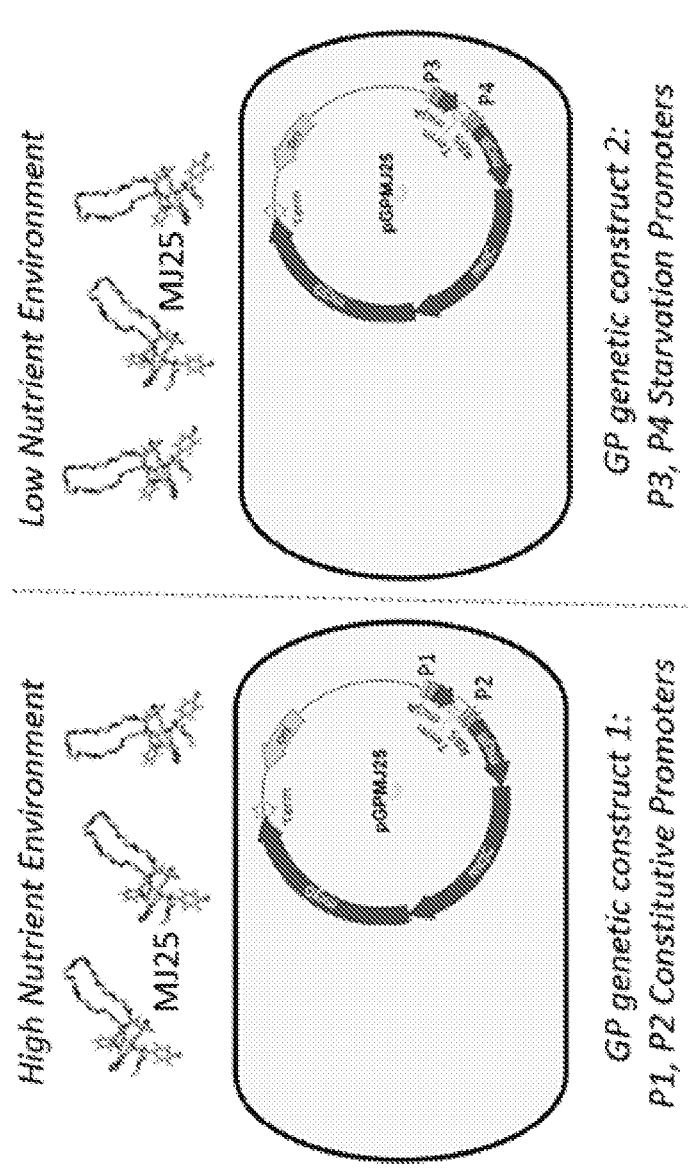
FIG. 10 shows detailed plasmid maps of probiotics engineered to express MJ25 under varying nutrient availability by exchange of promoters. The first probiotic expresses MJ25 out of promoter P1 and the modification and secretion genes (mcjB, mcjC, mcjD) out of promoter P2. The second probiotic expresses MJ25 out of promoter P3 and the modification and secretion genes (mcjB, mcjC, mcjD) out of promoter 4. The first probiotic contains a construct expressing MJ25 under constitutive promoters, P1 and P2 which are most active in high nutrient environments. The second probiotic contains a construct expressing MJ25 under starvation or low nutrient promoters, P3 and P4 which are most active in low nutrient environments.
Figure 11:
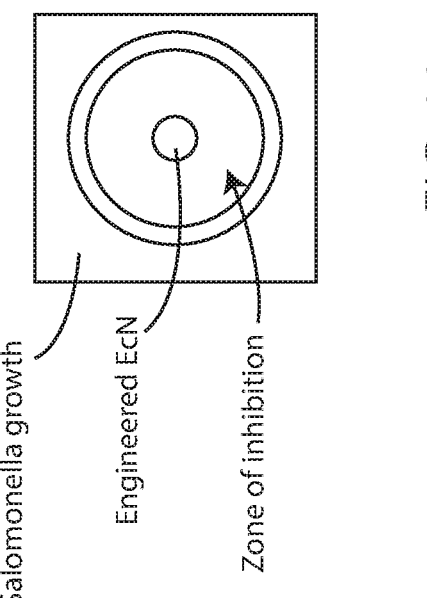
FIG. 11 shows the result of agar diffusion assays.

FIG. 11 shows the potent activity of *E. coli* Nissle 1917 (EcN) constitutively expressing Microcin J25 against *Salmonella Enteritidis* in an agar diffusion assay. To generate the modified EcN strain, EcN was transformed with our optimized constitutive system that results in the highest production in a high nutrient environment. This genetic construct contains promoters from the J23100 series. Specifically, J23100 was used as promoter P1, and J23106 as promoter P2 (see FIG. 10).

To test the activity of the modified EcN, molten rich medium (lysogeny broth) with agar was seeded with ~$10^6$ CFU/mL *Salmonella Enteritidis* and the plates were allowed to solidify. A colony of the modified EcN was swabbed then stabbed into the agar and incubated overnight at 37° C. FIG. 11 shows the result of this assay. The white dot at the center is the modified EcN. The light background indicates SE growth white the dark region is a zone of SE growth-inhibition resulting from MJ25 secreted by EcN. This example shows that engineered *E. coli* with pGPMJ25 shows high activity against strains of *Salmonella* in an agar diffusion assay in high nutrient agar.

Example 11: Methods for Assessing AMP Production: Supernatant Inhibition Assay (Results in TABLE 7)

To conduct these assays, colonies of the probiotics to be compared are inoculated in growth medium. Cultures are grown for 48 hours in an aerobic environment (shaking) at 37° C. After 48 hours, the cultures are centrifuged for one minute at 13,000×g to pellet the cells. The supernatant is then transferred to a new tube and boiled at 100° C. for sterilization.

Peptide concentration of the supernatants is then compared by serially diluting each supernatant and testing the dilutions abilities to inhibit the indicator strain, or a strain known to be susceptible to the peptides. This essentially estimates a minimal inhibitory concentration (MIC) of each supernatant. The supernatant with the lowest MIC is the most potent.

To determine the MIC, the indicator strain is grown overnight in rich medium. The following day, the indicator strain is diluted in rich medium to give ~$10^4$-$10^5$ CFU/mL. 30 μL of the probiotic supernatants are loaded into the first two rows of a sterile 96 well plate. 30 μL of phosphate buffered saline (PBS) is loaded into the remaining rows. 2× serial dilutions are performed from row 2 to row 8. 270 μL of the diluted indicator strain culture is then added to each well. This gives a series of 8 2× dilutions of supernatant giving concentrations from 10% v/v to 0.08% v/v.

The indicator plate is covered and incubated statically for 24 hours at 37° C. The following day, the last dilution exhibiting no growth is recorded for each supernatant tested. These data are then used to compare potency of each supernatant.

TABLE 7 shows the activities of four different probiotic organisms containing three different promoters (total of 12 probiotic strains) grown in low-nutrient growth medium (M9 minimal salts with 0.4% w/v glucose). Probiotic activities are shown as the reciprocal of the lowest percent supernatant capable of inhibiting the indicator strain, *Salmonella Enteritidis*. For example, 0.3% v/v (1/320×100) supernatant from probiotic #1 with the low nutrient promoter was sufficient to inhibit SE growth. The reciprocal is taken only to make the data more intuitive so that a higher value indicates a higher activity level.

From TABLE 7, one can see that under low nutrient conditions, the low-nutrient expression system generally exhibited superior activity compared to the constitutive or high nutrient expression system.

Example 12: Methods for Assessing AMP Production: Liquid Co-Culture Assay

FIG. 2 shows a graph of *Salmonella Enteritidis* growth in nutrient rich media (lysogeny broth, LB) over time comparing the effects of a probiotic producing MJ25 under high-nutrient conditions versus no treatment. This example shows that the probiotic engineered with a high nutrient promoter suppresses *Salmonella* growth in nutrient rich media.

A liquid co-culture assay was used to obtain these data. For this assay 10 μL of an overnight culture of SE was inoculated into 10 mL LB. For the group treated with the probiotic, 1 ml an overnight culture of probiotic was pelleted at 16100×g, and the supernatant was removed and replaced with fresh LB to ensure all activity was from peptide produced during co-culture with SE. After resuspension 5 ul uL of the probiotic was added to the freshly-inoculated SE culture. Three biological replicates were made for each untreated and probiotic-treated group (6 cultures total).

10 uL samples of each culture was taken at 0 hours, 6 hours, and 24 hours and serially diluted in a series of 6 10× dilutions. Dilutions were plated on selective agar (LB agar+ 30 µg/mL Nalidixic acid for SE). Plates were incubated overnight at 37° C. and colonies of SE were counted. Based on the number of colonies, the colony forming units (CFU) of SE per mL of culture were determined for each time point.

Example 13: Biomatrix Assays to Evaluate Engineered Probiotics Against Pathogens FIG. 2 shows the growth of *Salmonella Enteritidis* in a biomatrix assay in the presence of no probiotic, a probiotic expressing Microcin J25 under a constitutive promoter, or a probiotic expressing Microcin J25 under a promoter induced in low-nutrient environments. From these results, the constitutive promoter exhibits greater activity earlier in the incubation while the low-nutrient induced system is more potent after 24 hours. This is likely due to the depletion of nutrients over time which results in the induction of the low-nutrient system.

To conduct this assay, cecal contents are isolated from healthy birds that were sacrificed at a poultry research facility. Cecal contents are then diluted 2× with phosphate buffered saline (PBS) to facilitate sampling. 200 µL of cecal content is then inoculated with 0.5 uL of an overnight culture of SE grown in LB. When indicated, 0.5 uL of an overnight culture of the probiotic is also added to the cecal sample. These concentrations result in ~$10^6$ CFU SE/mL ceca and ~$10^6$ CFU probiotic/mL ceca.

In this example, either a high nutrient or low nutrient responsive engineered probiotic system, or a combination of both, or no probiotic at all was used. Note that the total amount of probiotic was maintained across all groups such that the combination treatment had a total of 0.5 uL probiotic culture added (0.25 uL high nutrient and 0.25 uL low nutrient probiotic.)

Samples were then incubated anaerobically at 37° C. and 10 µL aliquots were removed for analysis at 0 hours, 6 hours, and 24 hours. To enumerate SE, six 10× serial dilutions were performed for each 10 µL aliquot and dilutions were plated on selective agar (XLT4+25 µg/mL Nalidixic acid). Plates were incubated overnight at 37° C. and colonies were counted to obtain CFU SE/mL cecal content.

Example 14: Differing Expression of Proteins Under Different Gut Conditions

Another example of an engineered probiotic mixture would be the anaerobic responsive and stress-responsive system. Two probiotics are transformed with the GPMJ25 constructs. One construct includes an FNR promoter in P1 and P2 (SEQ ID NO: 6). The other construct includes osmB promoter in P1 and P2 (SEQ ID NO: 9). The former construct has highest activity in the parts of the GI tract in which oxygen is limited. The latter construct is useful for parts of the GI tract which are characterized by great osmotic stress such as bile acids present in the duodenum.

Example 15. Probiotic Administration in Birds

Birds were administered probiotic in the water daily for 28 days. Treatment included either a mixture of multiple strains (Nissle 1917, G5, G3/10, or G*, G5=33% of composition) or G5 only. Total CFU/mL water was identical for both treatment groups. On day 28, bird ceca were plated on selective agar to isolate and enumerate probiotic. Colonies were classified by strain-specific polymerase chain reaction.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A composition for treatment of an animal comprising a first genetically engineered bacterium comprising an exogenous polynucleotide comprising
    a first heterologous promoter;
    a first polynucleotide that encodes a first antimicrobial protein, wherein the first polynucleotide is operably linked to the first heterologous promoter; and
a second genetically engineered bacterium comprising an exogenous polynucleotide comprising
    a second heterologous promoter;
    a second polynucleotide that encodes a second antimicrobial protein, wherein the second polynucleotide is operably linked to the second heterologous promoter;

wherein the first heterologous promoter is directly or indirectly induced by one set of exogenous environmental conditions found in the gastrointestinal tract of the animal, and the second heterologous promoter is directly or indirectly induced by a second set of exogenous environmental conditions found in the gastrointestinal tract of the animal;

wherein at least one of the first genetically engineered bacterium and the second genetically engineered bacterium is *Bacillus subtilis* strain 168.

2. The composition of claim 1, wherein the first genetically engineered bacterium exhibits a colonization profile inside the gastrointestinal tract of animals and the second genetically engineered bacterium exhibits a different colonization profile inside the gastrointestinal tract of animals.

3. The composition of claim 1, wherein the first polynucleotide that encodes a first antimicrobial protein is different than the second polynucleotide that encodes a second antimicrobial protein.

4. The composition of claim 1, wherein the first heterologous promoter and the second heterologous promoter are selected to respond to different sigma factors selected from the group consisting of σ70 (RpoD), σ19 (FecI), σ24 (RpoE), σ28 (RpoF), σ32 (RpoH), σ38 (RpoS), and σ54 (RpoN).

5. The composition of claim 1, wherein the first heterologous promoter and the second heterologous promoter are selected to respond to different exogenous environmental conditions found in the gastrointestinal tract of animals, the exogenous environmental conditions defined by one or more of nutrient content, oxygen content, pH and bile concentration.

6. The composition of claim 1, wherein at least one of the first heterologous promoter and the second heterologous promoter are selected from the group of constitutive promoters, exogenously-inducible promoters, pH-inducible promoters, osmotic pressure-inducible promoters, anaerobically-inducible promoters, starvation-inducible promoters, temperature-inducible promoters, inflammation-inducible promoters, and quorum-sensing promoters.

7. The composition of claim 1, wherein at least one of the first heterologous promoter and the second heterologous promoter are selected from the group of rpoS promoters, anaerobically-inducible promoters, chloride-inducible promoters, and stationary-phase promoters.

8. The composition of claim 1, wherein the first genetically engineered bacterium and the second genetically engineered bacterium are probiotic bacteria.

9. The composition of claim 1, wherein the first genetically engineered bacterium and the second genetically engineered bacterium are selected from the group consisting of *Bacillus, Bacteroides, Bifidobacterium, Clostridium, Escherichia, Lactobacillus,* and *Lactococcus.*

10. The composition of claim 1, wherein at least one of the first genetically engineered bacterium and the second genetically engineered bacterium are *Escherichia coli* strain Nissle.

11. The composition of claim 1, wherein the first antimicrobial protein and the second antimicrobial protein are selected from the group consisting Microcin J25, Microcin V, Microcin L, Microcin N, Enterocin A, Enterocin B, Enterocin P, and Hiracin JM79, or conservative variants thereof.

12. The composition of claim 1, wherein the heterologous promoters and the polynucleotides that encode the antimicrobial proteins are located on the chromosome of the bacterium.

13. The composition of claim 1, wherein the heterologous promoters and the polynucleotides that encode the antimicrobial proteins are located on a plasmid in the bacterium.

* * * * *